United States Patent [19]

Carr et al.

[11] Patent Number: 5,380,731
[45] Date of Patent: Jan. 10, 1995

[54] ANTIALLERGIC COMPOUNDS

[75] Inventors: Albert A. Carr; John M. Kane; Hsien C. Cheng, all of Cincinnati, Ohio

[73] Assignee: Merrell Dow Pharmaceuticals Inc., Cincinnati, Ohio

[21] Appl. No.: 108,786

[22] Filed: Aug. 17, 1993

Related U.S. Application Data

[63] Continuation of Ser. No. 984,715, Dec. 2, 1992, abandoned, which is a continuation of Ser. No. 793,073, Nov. 15, 1991, abandoned, which is a continuation of Ser. No. 627,687, Dec. 14, 1990, abandoned.

[51] Int. Cl.⁶ .................. A61K 31/445; C07D 401/06
[52] U.S. Cl. ...................................... 514/322; 546/199
[58] Field of Search .................. 546/199; 514/322

[56] References Cited

U.S. PATENT DOCUMENTS

| | | | |
|---|---|---|---|
| 4,219,559 | 8/1980 | Janssens et al. | 424/267 |
| 4,857,536 | 8/1989 | Manoury et al. | 514/322 |
| 4,908,372 | 3/1990 | Carr et al. | 514/322 |
| 4,929,618 | 5/1990 | Koda et al. | 514/253 |
| 4,943,580 | 7/1990 | Janssens et al. | 514/303 |
| 4,971,980 | 11/1990 | Giani et al. | 514/322 |
| 5,064,840 | 11/1991 | Carr et al. | 514/322 |
| 5,322,850 | 6/1994 | Orjales-Vemero et al. | 514/322 |

FOREIGN PATENT DOCUMENTS

| | | |
|---|---|---|
| 0151826 | 8/1985 | European Pat. Off. . |
| 0363963 | 12/1989 | European Pat. Off. . |
| WO9206086 | 4/1992 | European Pat. Off. . |

OTHER PUBLICATIONS

Journal of Organic Chemistry, vol. 55, No. 4; 16 Feb. 1990, pp. 1399-1401.

Primary Examiner—Glennon H. Hollrah
Assistant Examiner—Brian M. Burn
Attorney, Agent, or Firm—J. Michael Dixon

[57] ABSTRACT

The present invention is directed to a new class of piperidinyl benzimidazoles that are useful in the treatment of allergic disorders.

44 Claims, No Drawings

ANTIALLERGIC COMPOUNDS

CROSS-REFERENCE TO RELATED APPLICATION

This is a continuation of application Ser. No. 07/984,715, filed Dec. 2, 1992, now abandoned, which is a continuation of Ser. No. 07/793,073, filed Nov. 15, 1991, now abandoned, which is a continuation of Ser. No. 07/627,687, filed Dec. 14, 1990, now abandoned.

The present invention is directed to a new class of piperidinyl benzimidazole derivatives and their use in the treatment of allergic disorders. Another aspect of the invention is directed to pharmaceutical compositions containing these substances.

In accordance with the present invention, a new class of piperidinyl benzimidazoles have been discovered which can be described by the following formula:

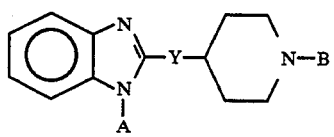

FORMULA I in which Y is represented by CO or CHOH; A and B are each independently represented by a substituent selected from the group consisting of:

a) a carbonyl derivative of the formula $-(CH_2)_n-Z-(CH_2)_mCOR_1$ in which n and m are each independently represented by an integer from 0–3, Z is represented by a bond, O, or S and $R_1$ is represented by OH, a $C_1-C_4$ alkoxy or $-NR_2R_3$ wherein $R_2$ and $R_3$ are each independently represented by H or $C_1-C_4$ alkyl;

b) an amido tetrazole derivative of the formula:

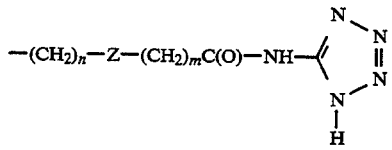

wherein n, m and Z are as previously defined;

c) an alkyl derivative of the formula $-(CH_2)_n-Z-(CH_2)_mCH_3$ wherein n, m and Z are as previously defined;

d) an alkyl tetrazole of the formula:

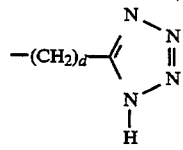

in which d is represented by an integer from 1–5;

e) an aralkyl derivative of the formula

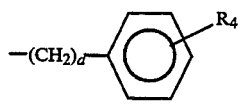

in which $R_4$ is represented by a substituent selected from the group consisting of H, $C_1-C_4$ alkyl, $C_1-C_4$ alkoxy, OH, halogen, and $-CF_3$, and d is as previously defined, f) an oxo derivative of the formula: $-C(O)R_5$, in which $R_5$ is represented by a $C_1-C_4$ alkyl, $C_1-C_4$ alkoxy, $-CF_3$ or $-NR_2R_3$, wherein $R_2$ and $R_3$ are as previously defined; and g) hydrogen and the pharmaceutically acceptable salts thereof, with the proviso's: 1) that A and B are not both simultaneously aralkyl 2) that when B is an oxo derivative in which $R_5$ is $C_1-C_4$ alkoxy, then A is not aralkyl, 3) when A and/or B is a carbonyl derivative in which Z is a bond, then the sum of m and n is at least one 4) B is not hydrogen when A is aralkyl and 5) A is not hydrogen.

The compounds of Formula I are useful in the treatment of allergic diseases. They antagonize the effect of histamine at the $H_1$ receptor. They are PAF antagonists. They also inhibit the release of histamine, leukotrienes, and other autocoids from sensitized mast cells.

DETAILED DESCRIPTION OF THE INVENTION

As used in the this application:

a) the term "halogen" refers to a fluorine, chlorine, or bromine atom;

b) the term "Hal" or "halide" refers to a chlorine, bromine, or an iodide atom;

c) the term "$C_1-C_4$ alkyl" refers to a branched or straight chained alkyl group containing from 1–4 carbon atoms, such as methyl, ethyl, n-propyl, isopropyl, n-butyl, isobutyl and t-butyl;

d) the term "$C_1-C_4$ alkoxy" refers to a straight or branched alkoxy group containing from 1–4 carbon atoms, such as methoxy, ethoxy, n-propoxy, isopropoxy, n-butoxy, isobutoxy and t-butoxy;

e) the term "$-C(O)-$" refers to a carbonyl group having the following structure:

f) the term "CHOH" refers to a hydroxymethylene group;

g) the term "aralkyl derivative" refers to:

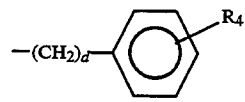

h) the term "amido tetrazole" refers to a substituent of the formula:

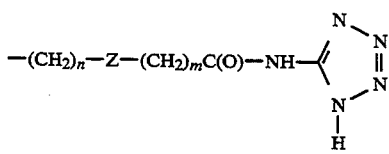

i) the term "alkyl tetrazole" refers to the following substituent:

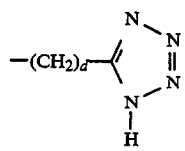

j) the term "carbonyl derivative" refers to the following substituent: —(CH$_2$)$_n$—Z—(CH$_2$)$_m$COR$_1$
k) the term "alkyl derivative" refers to the following substituent: —(CH$_2$)$_n$—Z—(CH$_2$)$_m$CH$_3$
l) the term "oxo derivative" refers to the following substituents: —C(O)R$_5$.
m) the term "tet" refers to a tetrazole of the following structure:

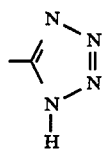

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and various substituted pyridines.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases or resolution via chiral salt formation and subsequent separation by selective crystallization following recovery of the salt form by the usual methods. Alternatively utilization of a specific optical isomer as the starting material will produce the corresponding isomer as the final product.

The piperidinyl benzimidazoles of this invention always contain a substituent (A) at the 1-position of the benzimidazole nucleus and a substituent at the 1-position of the piperidinyl ring (B). These substituents may be the same or different. However, A and B should not both be represented by aralkyl derivatives at the same time. In the compounds of Formula I in which either A or B is represented by an aralkyl derivative, the phenyl ring of this aralkyl derivative may be optionally substituted as indicated by the R$_4$ substituent. R$_4$ may be represented by up to 3 non-hydrogen substituents. These substituents may be located at any of the ortho, meta, or para positions. These substituents may be the same or different. In the compounds of Formula I in which either A and/or B are represented by carbonyl derivatives in which R$_1$ is NR$_2$R$_3$ or oxo derivatives in which R$_5$ is represented by NR$_2$R$_3$, R$_2$ and R$_3$ may be represented by the same substituents or different substituents.

The piperidinyl benzimidazole derivatives of Formula I can be prepared by utilizing conventional procedures and techniques which are well known and appreciated in the art.

A general synthetic procedure for the preparation of compounds of Formula I wherein A is either an alkyl derivative or an aralkyl derivative and B is either a carbonyl derivative, an alkyl derivative, an oxo derivative, an aralkyl derivative or a hydrogen is set forth in Scheme A. In Scheme A, all substituents, unless otherwise indicated, are as previously defined.

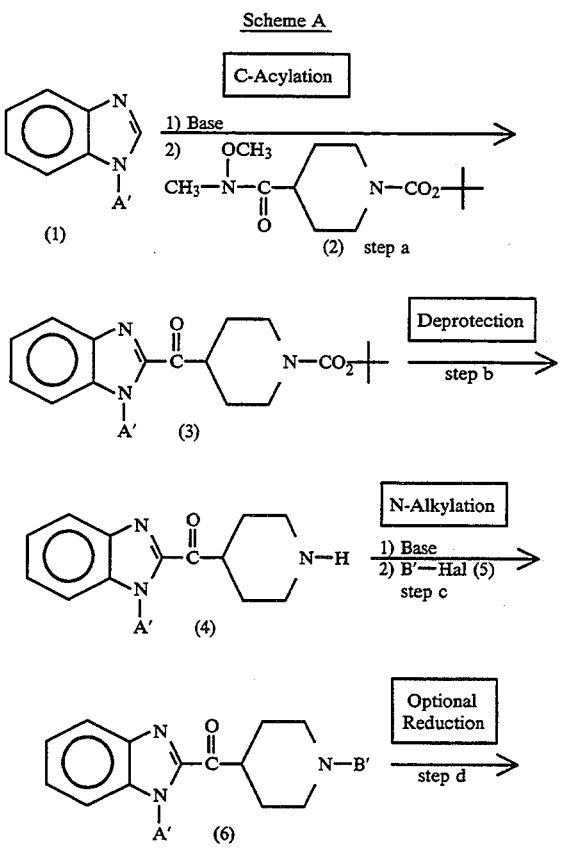

-continued
Scheme A

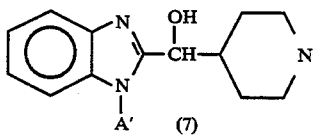

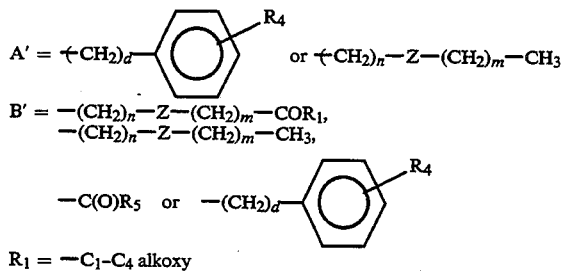

$R_1 = -C_1-C_4$ alkoxy

In general, an appropriate piperidinyl benzimidazole derivative of Formula I in which A is either an alkyl derivative or an aralkyl derivative and B is either a carbonyl derivative, an alkyl derivative, an aralkyl derivative, an oxo derivative or a hydrogen, wherein all substituents, unless otherwise indicated, are as previously defined, can be prepared in a multi-step process.

In step a, the appropriate N-alklylated benzimidazole of structure (1) is acylated with the piperidinyl derivative of structure (2) under basic conditions to give the piperidinyl benzimidazole derivative of structure (3).

For example, a solution of the benzimidazole derivative of structure (1) is contacted with an organolithium compound such as n-butyllithium or t-butyllithium, more preferably with t-butyllithium, for a period of time ranging from about 5 minutes to about 30 minutes and more preferably about 15 minutes; at a temperature range of from about −90° C. to about −50° C. and more preferably about −78° C. The organolithium compound will be present in the quantity of from about 1.0 to about 1.1 equivalents for every mole of benzimidazole derivative utilized, and more preferbly will be present in an approximately equimolar quantity with the benzimidazole derivative. The reaction is typically conducted under anhydrous conditions in a suitable aprotic organic solvent such as tetrahydrofuran.

The piperidinyl derivative of Formula (2) is then added to the reaction medium and the reaction medium is warmed from about −78° C. to about 0° C. The piperidinyl derivative and the benzimidazole derivative are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 30 minutes. The reaction is then quenched with a proton source such as, for example, saturated aqueous ammonium chloride or methanol. The resulting reaction mixture is extracted with a suitable solvent, such as ethyl acetate, washed with water, dried over either Na₂SO₄ or MgSO₄, filtered and the solvent evaporated in vacuo.

The piperidinyl benzimidazole of structure (3) can be purified according to techniques known in the art. For example, one suitable technique is to subject the concentrate obtained above to chromatography utilizing an appropriate organic solvent such as ethyl acetate as the eluting agent. The eluent can be evaporated and the resulting product can be recrystallized from a suitable solvent such as, for example, cyclohexane. Other suitable solvent systems will be readily apparent to those skilled in the art.

In step b, the piperidine functionality of the piperidinyl benzimidazole of structure (3) is deprotected under acidic conditions to give the piperidinyl benzimidazole of structure (4) using procedures and techniques well known in the art. For example, the t-butyloxycarbonyl group (t-BOC) can be cleaved with trifluoroacetic acid.

In step c, the piperidine functionality of the piperidinyl benzimidazole of structure (4) is N-alkylated under basic conditions with the appropriate alkyl halide of structure (5) to give the piperidinyl benzimidazole of structure (6). For example, the piperidinyl benzimidazole of structure (4) is reacted with the appropriate alkyl halide of structure (5) in the presence of a base such a $K_2CO_3$, $KHCO_3$, $Na_2CO_3$, $NaHCO_3$, triethylamine, or pyridine. Typically the reactants will be stirred together for a period of time ranging from about 30 minutes to about 48 hours, at a temperature range of from about 0° C. to about 100° C. The non-reacting substituents appearing in the alkyl halide correspond to those appearing in the product. The piperidinyl benzimidazole of structure (6) can be recovered from the reaction zone by treatment with water and extraction with an organic solvent as is known in the art. It can be purified by techniques known in the art such as recrystallization or chromatography as described previously. Typically the piperidinyl benzimidazole of structure (4), as its trifluoracetic acid salt, is converted in situ to its free base during the alkylation. However, in the case where the alkyl halide of structure (5) is represented by Hal—C(O)—NR₂R₃, the piperidinyl benzimidazole of structure (4) must be converted to its free base prior to addition of the alkyl halide to avoid formation of undesired products.

In optional step d, the carbonyl functionality of the piperidinyl benzimidazole of structure (6) can be reduced to the corresponding hydroxymethylene group by techniques well known in the art. For example, one suitable technique is to react the piperidinyl benzimidazole of structure (6) with a reducing agent, such as sodium borohydride, in a suitable solvent such as ethanol. The piperidinyl benzimidazole of structure (6) and the reducing agent are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 30 minutes. The solvent is removed under vacuum and the piperidinyl benzimidazole of structure (7) can be recovered from the reaction zone by treatment with water and extraction with an organic solvent as is known in the art. It can be purified by techniques known in the art such as recrystallization or chromatography as described previously in step a.

In addition, those piperidinyl benzimidazole compounds of structures (6) or (7), in which B' is represented by a carbonyl derivative of the formula —(CH₂)ₙ—Z—(CH₂)ₘCOR₁, wherein R₁ is C₁-C₄ alkoxy, can be further functionalized by hydrolyzing the ester functionality using techniques and procedures well known in the art. For example, the ester functionality may be hydrolyzed by treating the piperidinyl benzimidazole compounds of structures (6) or (7) with an aqueous base. Following neutralization, the resulting piperidinyl benzimidazole of structure (6) or (7), wherein $R_1$ is hydroxy, can be recovered from the reaction zone using techniques known in the art such as crystallization or ion exchange chromatography.

Further optional functionalization of the free carboxylic acid to an amide derivative wherein $R_1$ is $-NR_2R_3$ can be accomplished using techniques and procedures well known and appreciated in the art. For example, the free carboxylic acid, derived from (6), can be activated by conversion to its imidazolide using 1,1'-carbonyldiimidazole, in a suitable aprotic solvent system, such as dimethylformamide and tetrahydrofuran. The activation reaction is typically conducted under an inert atmosphere such as argon and is stirred at room temperature for a period of time ranging form 2-5 hours. The appropriate amine, represented by the formula $HNR_2R_3$, in which $R_2$ and $R_3$ are as previously defined, is then added and the reaction is typically reacted for a period of time ranging from 2-5 hours and at a temperature range of from room temperature to reflux. The reaction mixture is then concentrated to a residue, dissolved in water and treated with hydrochloric acid until a pH of 6 is obtained. The resulting solid is then purified by recrystallization or chromatography as described previously. It is understood that other well known methods for converting carboxylic acids to amides may also be used, such as forming an acid chloride with thionyl chloride in a suitable aprotic solvent such as methylene chloride, followed by reaction with the appropriate amine of formula $HNR_2R_3$.

Similarly, optional functionalization of the free carboxylic acid to another ester derivative wherein $R_1$ is $C_1$–$C_4$ alkoxy can be accomplished using techniques and procedures well known and appreciated in the art. For example, the free carboxylic acid of structure (6) may be converted to its acid chloride with thionyl chloride in a suitable aprotic solvent, such as methylene chloride, followed by reaction with the appropriate alcohol and an appropriate acid scavenger such as triethylamine. The products can be purified by techniques known in the art such as recrystallization or chromatography as described previously in step a.

Such amides, carboxylic acids and esters of structure (6) can then be reduced to the corresponding alcohols of structure (7) by the methods described previously in optional step d.

The starting materials for use in the general synthetic procedure outlined in Scheme A are readily available to one of ordinary skill in the art. For example, certain benzimidazole derivatives of structure (1) are described in U.S. Pat. No. 4,908,372 (Mar. 13, 1990). The intermediate described by Structure 2 is disclosed in U.S. patent application No. 07/736,194 (now U.S. Pat. No. 5,134,149) which is hereby incorporated by reference.

The following examples present typical syntheses as described by Scheme A. These examples are understood to be illustrative only and are not intended to limit the scope of the invention in any way. As used in the following examples, the following terms have the meanings indicated: "g" refers to grams, "mmol" refers to millimoles, "mL" refers to milliliters, "° C." refers to degrees Celsius, "TLC" refers to thin layer chromatography, "mg" refers to milligrams, "µL" refers to microliters.

EXAMPLE 1

1-[[(2-Ethoxy)ethyl]-1H-benzimidazol-2-yl][1-[2-(4-methoxyphenyl)ethyl]-4-piperidinyl]methanone hydrochloride The purpose of this example is to demonstrate one method for the preparation of a piperidinyl benzimidazole of Formula I wherein A is an alkyl derivative and B is an aralkyl derivative.

Step a:

1-[[(2-Ethoxy)ethyl]-1H-benzimidazol-2-yl][1-(t-butyloxycarbonyl)-4-piperidinyl]methanone Mix benzimidazole (11.8 g, 0.1 mol) and dimethylformamide (20 mL) and place under an argon atmospere. Cool to 0° C. with an ice-water bath and add, in portions, sodium hydride (3.3 g, 0.11 mol). Remove the ice-water bath and stir for 30 minutes. Add, by dropwise addition, 2-chloroethyl ethyl ether (11.1 mL, 0.101 mol) and stir at room temperature overnight. Quench with water and partition between water and a 2/1 mixture of ethyl acetate/toluene. Separate the organic phase, wash with water (2×), then with brine (1×) and dry ($MgSO_4$). Filter off the drying agent and evaporate the solvent in vacuo to give 14 g of the crude product. Purify by flash chromatography (20% acetone/methylene chloride) to give a yellow oil. Purify further by distillation to give 1-[[(2-ethoxy)ethyl]-1H-benzimidazol] as a colorless oil; bp 170° C. @0.02 mm Hg.

Anal. Calcd for $C_{11}H_{14}N_2O \cdot 0.3H_2O$: C, 67.53; H, 7.52; N, 14.32; Found: C, 67.54, H. 7.52; N, 14.73.

Mix 1-(2-ethoxy)ethyl-1H-benzimidazole (10.8 g, 56.52 mmol) and tetrahydrofuran (100 mL) under an argon atmosphere. Cool in a dry ice/isopropanol bath to approximately $-78°$ C. Add, by dropwise addition, t-butyllithium (36.6 mL of a 1.7M solution in pentane, 62.2 mmol) and stir for 20 minutes. Add a solution of N-(t-butyloxycarbonyl)-4-(N-methyl-N-methoxy carboxamide)-piperidine (15.39 g, 56.52 mmol) in tetrahydrofuran (100 mL). Stir at $-78°$ C. for 2.5 hours, quench with methanol (20 mL), remove the ice-bath and allow to warm to room temperature. Quench with saturated aqueous ammonium chloride (100 mL). Partition between water and ethyl acetate, separate the organic phase and extract the aqueous phase with ethyl acetate (2×). Combine the organic phases and wash with brine. Dry ($Na_2SO_4$) overnight, filter off the drying agent and remove the solvent in vacuo. Purify by flash chromatography (ethyl acetate) to give the crude product. Purify further by flash chromatography (25% ethyl acetate/hexane) to give the title compound as a white solid. Recrystallize (cyclohexane/hexane) a sample and dry at 25° C. @1 mm Hg for 16 hours for elemental analysis; mp 96°–98° C. This compound exhibited a pA2 value of 6.22 in the guinea pig ileum screen described on pages 66 and 67 of this application using the method of Van Rossum.

Anal. Calcd for $C_{22}H_{31}N_3O_4$: C, 65.82; H, 7.78; N, 10.48; Found: C, 65.97; H, 8.07; N, 10.48.

Step b:

1-[[(2-Ethoxy)ethyl]-1H-benzimidazol-2-yl][1-(4-piperidinyl)]methanone, trifluoroacetic acid salt Mix 1-[[(2-ethoxy)ethyl]-1H-benzimidazol-2-yl][1-(t-butyloxycarbonyl)-4-piperidinyl]methanone (10.71 g, 26.67 mmol) and trifluoroacetic acid (75 mL). Stir at room temperature for 2 hours. Triturate with ethyl ether/hexane with ice-water cooling. Filter the resulting white solid and wash with hexane to give the title compound. Dry a sample at 25° C. @1 mm Hg for 16 hours for elemental analysis; mp 136°-38° C.

Anal. Calcd for $C_{17}H_{23}N_3O_2 \cdot CF_3CO_2H$: C, 55.84; H, 5.82; N, 10.12; Found: C, 54.74; H, 5.89; N. 9.96.

Step c:
1-[[(2-Ethoxy)ethyl]-1H-benzimidazol-2-yl][1-[2-(4-methoxyphenyl)ethyl]-4-piperidinyl]methanone hydrochloride Mix 1-[[(2-ethoxy)ethyl]-1H-benzimidazol-2-yl][1-(4-piperidinyl)]methanone, trifluoroacetic acid salt (3.5 g, 8.43 mmol), (1-methoxy)-4-(2-bromoethyl)benzene (1.9 g, 8.85 mmol), potassium carbonate (2.91 g, 21.08 mmol) and dimethylformamide (50 mL). Stir and heat at 90° C. overnight. Allow to cool to room temperature, dilute with water and extract with 2:1 ethyl acetate/toluene (2×). Wash the combined organic phases with water (3×), then brine and dry (MgSO$_4$). Filter and evaporate the solvent in vacuo to give a brown oil. Purify by flash chromatography (ethyl acetate) to give 2.5 g yellow-orange oil. Dissolve the oil in ethanol/ethyl ether, treat with charcoal and filter. Add ethereal hydrochloric acid until acidic and cool overnight. Filter the solid, wash with ethyl ether. Recrystallize (2-butanone/t-butylmethyl ether) a sample to give an off-white solid; mp 154°-56° C. This compound exhibited a pA2 value of 9.39 in the guinea pig ileum screen described on pages 66 and 67 of this application using the method of Van Rossum.

Anal. Calc for $C_{26}H_{33}N_3O_3 \cdot HCl \cdot 0.25H_2O$: C, 65.53; H, 7.30; N, 8.82; Found: C, 65.55; H, 7.48; N, 8.72.

EXAMPLE 2

1-[[(4-Fluorophenyl)methyl]-1H-benzimidazol-2-yl][1-(carbomethoxy methoxyethyl)-4-piperidinyl]methanone The purpose of this example is to demonstrate one method for the preparation of a piperidinyl benzimidazole of Formula I wherein A is an aralkyl derivative and B is a carbonyl derivative.

Step a:
1-[[(4-Fluorophenyl)methyl]-1H-benzimidazol-2-yl][1-(t-butyloxycarbonyl)-4-piperidinyl]methanone Mix 1-(4-fluorophenyl)methyl-1H-benzimidazole (1.21 g, 5.68 mmol) and tetrahydrofuran (25 mL). Cool in a dry ice/isopropanol bath to approximately −78° C. Add, by dropwise addition, t-butyllithium (3.68 mL of a 1.7M solution in pentane, 6.25 mmol) and stir for 20 minutes. Add a solution of N-(t-butyloxycarbonyl)-4-(N-methyl-N-methoxy carboxamide)-piperidine (1.55 g, 5.68 mmol) in tetrahydrofuran (100 mL). Stir at −78° C. for 3 hours, remove the ice-bath and allow to warm to room temperature. Quench with saturated aqueous ammonium chloride. Partition between water and ethyl acetate, separate the organic phase and extract the aqueous phase with ethyl acetate (2×). Combine the organic phases and wash with brine. Dry (Na$_2$SO$_4$) overnight, filter off the drying agent and remove the solvent in vacuo. Purify by flash chromatography (25% ethyl acetate/hexane) to give the crude product. Recrystallize (cyclohexane/hexane) to give the title compound as white crystals; mp 114°-15° C. This compound exhibited a pA2 value of less than 7 in the guinea pig ileum screen described on pages 66 and 67 of this application using the method of Van Rossum.

Anal. Calcd for $C_{25}H_{28}FN_3O_3$: C, 68.63; H, 6.45; N, 9.60; Found: C, 68.63; H, 6.49; N, 9.50.

Step b:
1-[[(4-Fluorophenyl)methyl]-1H-benzimidazol-2-yl][1-(4-piperidinyl)]methanone, trifluoroacetic acid salt Mix 1-[[(4-fluorophenyl)methyl]-1H-benzimidazol-2-yl][1-(t-butyloxycarbonyl)-4-piperidinyl]methanone (1.65 g, 3.77 mmol) and trifluoroacetic acid (10 mL). Stir at room temperature for 30 minutes. Dilute with ethyl ether (150 mL) and cool the mixture in an ice bath. Collect the precipitate by filtration and wash with ethyl ether, then dry by suction. Recrystallize (ethanol/ethyl ether) to give the title compound as colorless needles; mp 213°-15° C.

Anal. Calcd for $C_{20}H_{20}FN_3O \cdot CF_3CO_2H$: C, 58.54; H, 4.69; N, 9.31; Found: C, 58.55, H, 4.77; N, 9.29.

Step c:
1-[[(4-Fluorophenyl)methyl]-1H-benzimidazol-2-yl][1-(carbomethoxy methoxyethyl)-4-piperidinyl]methanone Mix 1-[[(4-fluorophenyl)methyl]-1H-benzimidazol-2-yl][1-(4-piperidinyl)]methanone, trifluoroacetic acid salt (5.83 g, 12.91 mmol), carbomethoxy methoxyethyl bromide (3.0 g, 15.3 mmol), potassium carbonate (5.29 g, 38.25 mmol) and dimethylformamide (100 mL). Stir and heat and at 90° C. overnight. Allow to cool to room temperature, dilute with water and extract with 2:1 ethyl acetate/toluene (2×). Wash the combined organic phases with water (3×), then brine and dry (MgSO$_4$). Evaporate the solvent in vacuo to give an oil. Purify by flash chromatography (10% methanol/ethyl acetate) to give a yellow-brown waxy solid. Recrystallize (cyclohexane/hexane) to give the title compound as a white powder; mp 85°-6° C. This compound exhibited a pA2 value of 8.75 in the guinea pig ileum screen described on pages 66 and 67 of this application using the method of Schild.

Anal. Calc for $C_{25}H_{28}FN_3O_4$: C, 66.21; H, 6.22; N, 9.27; Found: C, 66.11; H, 6.21; N, 9.20.

EXAMPLE 3

1-[[(4-Fluorophenyl)methyl]-1H-benzimidazol-2-yl][1-(carbo-t-butyoxymethyl)-4-piperidinyl]methanone The purpose of this example is to demonstrate another preparation of a piperidinyl benzimidazole of Formula I wherein A is an aralkyl derivative and B is a carbonyl derivative.

Mix 1-[[(4-fluorophenyl)methyl]-1H-benzimidazol-2-yl][1-(4-piperidinyl)]methanone, trifluoroacetic acid salt (4.0 g, 8.86 mmol), t-butyl bromoacetate (1.9 g, 9.74 mmol), potassium hydrogen carbonate (2.2 g, 22 mmol), tetrahydrofuran (129 mL) and water (30 mL). Stir and heat at reflux for 4 hours. Allow to cool to room temperature and concentrate to ½ volume. Dilute with water the extract with ethyl ether (2×). Wash the combined organic phases with water (3×), then brine and dry (MgSO$_4$). Evaporate the solvent in vacuo to give a colorless oil. Purify by flash chromatography (30% ethyl acetate/hexane) to give an orange oil. Recrystallize (cyclohexane/hexane) a sample to give the title compound as a yellow powder; mp 129°-31° C.

Anal. Calc for $C_{26}H_{30}FN_3O_3 \cdot 0.2C_6H_{12}$: C, 69.75; H, 6.97; N, 8.97; Found: C, 69.72; H, 7.14; N, 9.11.

EXAMPLE 4

1-[[(4-Fluorophenyl)methyl]-1H-benzimidazol-2-yl][1-(carboxymethyl)-4-piperidinyl]methanone The purpose of this example is to demonstrate another preparation of a piperidinyl benzimidazole of Formula I wherein A is an aralkyl derivative and B is a carbonyl derivative.

Dissolve 1-[[(4-fluorophenyl)methyl]-1H-benzimidazol-2-yl][1-(carbo-t-butoxy methyl)4-piperidinyl]methanone (500 mg, 1.11 mmol) in trifluoroacetic acid (2 mL) and stir for 2 hours. Evaporate the solvent in vacuo to give an oil. Dissolve the oil in a minimum amount of methanol, dilute with water and place on an ion-exchange column (Bio-Rad cation exchange resin, AG 50W-X8, 200–400 mesh, hydrogen form) and elute with water until neutral, then with 1N ammonium hydroxide. Combine the basic fractions and evaporate. Crystallize (water, 10 mL) the residue to give the title compound as fluffy yellow crystals; mp 172°–6° C. This compound exhibited a pA2 value of 8.63 in the guinea pig ileum screen using the method of Van Rossum.

Anal. Calc for $C_{22}H_{22}FN_3O_3$: C, 66.82; H, 5.61; N, 10.63; Found: C, 66.53; H, 5.55; N, 10.62.

EXAMPLE 5

1-[[(4-Fluorophenyl)methyl]-1H-benzimidazol-2-yl][1-(ethoxycarbonyl)-4-piperidinyl]methanone The purpose of this example is to demonstrate another preparation of a piperidinyl benzimidazole of Formula I wherein A is an aralkyl derivative and B is a carbonyl derivative.

Dissolve 1-[[(4-fluorophenyl)methyl]-1H-benzimidazol-2-yl][1-(carboxymethyl)4-piperidinyl]methanone, trifluoroacetic acid salt (3.00 g, 6.65 mmol) in pyridine (60 mL) and add, by dropwise addition, ethyl chloroformate (0.70 mL, 7.3 mmol). Stir for 64 hours, evaporate the pyridine in vacuo and dissolve the residue in a two-phase mixture of ethyl acetate/water. Separate the organic phase and extract the aqueous phase with ethyl acetate (2×). Combine the organic phases, wash with water and saturated aqueous sodium chloride. Dry (MgSO4), filter and evaporate the filtrate in vacuo to give an oil. Purify by silica gel chromatography (50% ethyl acetate/hexane) and crystallize (cyclohexane/hexane) to give the title compound as a colorless solid; mp 92°–96° C.

Anal. Calc for $C_{23}H_{24}FN_3O_3$: C, 67.47; H, 5.91; N, 10.26; Found: C, 67.28; H, 5.96; N, 10.08.

EXAMPLE 6

1-[[(4-Fluorophenyl)methyl]-1H-benzimidazol-2-yl][1-(N,N-diethylcarbamoyl)-4-piperidinyl]methanone The purpose of this example is to demonstrate one method for the preparation of a piperidinyl benzimidazole of Formula I wherein A is an aralkyl derivative and B is an oxo derivative.

Place 1-[[(4-fluorophenyl)methyl]-1H-benzimidazol-2-yl][1-(4-piperidinyl)]methanone, trifluoroacetic acid salt (4.02 g, 8.9 mmol) in a sepatory funnel and partition between ethyl acetate and 10% aqueous potassium hydroxide. Separate the organic phase and extract the aqueous phase with additional ethyl acetate. Wash the combined organic phases with brine and dry (Na2SO4). Evaporate the solvent in vacuo to give 1-[(4-fluorophenyl)methyl]-1H-benzimidazol-2-yl][1-(4-piperidinyl)]methanone as yellow crystals.

Mix 1-[[(4-fluorophenyl)methyl]-1H-benzimidazol-2-yl][1-(4-piperidinyl)]methanone (2.68 g, 7.94 mmol) and pyridine (50 mL). Add, by dropwise addition, diethyl carbamoyl chloride (1.1 mL 8.68 mmol) and stir overnight. Remove excess pyridine in vacuo and dissolve the residue in a two-phase mixture of ethyl acetate/1N hydrochloric acid. Separate the organic phase and extract the aqueous phase with additional ethyl acetate (2×). Wash the combined organic phases with saturated aqueous sodium hydrogen carbonate, then with brine and dry (Na2SO4). Evaporate the solvent in vacuo to give an orange oil. Purify by flash chromatography (30% ethyl acetate/methylene chloride) to give the title compound as a viscous yellow oil. This comound exhibited a pA2 value of 7.7 in the guinea pig ileum screen using the method of Van Rossum.

Anal. Calc for $C_{25}H_{29}FN_4O_4$: C, 68.79; H, 6.70; N, 12.83; Found: C, 68.92; H, 6.72; N, 12.75.

EXAMPLE 7

1-[[(4-Fluorophenyl)methyl]-1H-benzimidazol-2-yl-][1-(acetyl)-4-piperidinyl]methanone The purpose of this example is to demonstrate another preparation of a piperidinyl benzimidazole of Formula I wherein A is an aralkyl derivative and B is an oxo derivative.

Mix 1-[[(4-fluorophenyl)methyl]-1H-benzimidazol-2-yl][1-(4-piperidinyl)]methanone, trifluoroacetic acid salt (3.0 g, 6.65 mmol) and pyridine (60 mL). Add, by dropwise addition, acetyl chloride (0.52 mL, 7.3 mmol) and stir overnight. Remove excess pyridine in vacuo and dissolve the residue in a two-phase mixture of ethyl acetate/water. Separate the organic phase and extract the aqueous phase with additional ethyl acetate (2×). Wash the combined organic phases with water, then with brine and dry (MgSO4). Evaporate the solvent in vacuo give a foam. Purify by flash chromatography (ethyl acetate) to give the crude product as a solid. Recrystallize (ethyl acetate) to give the title compound as white crystals; mp 161°–3° C. This compound exhibited a pA2 value of less than 7 in the guinea pig ileum screen described on pages 66 and 67 of this application using the method of Van Rossum.

Anal. Calc for $C_{22}H_{22}FN_3O_2$: C, 69.64; H, 5.84; N, 11.02; Found: C, 69.83; H, 5.96; N, 11.06.

EXAMPLE 8

1-[[(4-Fluorophenyl)methyl]-1H-benzimidazol-2-yl][1-(trifluoroacetyl)-4-piperidinyl]methanone The purpose of this example is to demonstrate another preparation of a piperidinyl benzimidazole of Formula I wherein A is an aralkyl derivative and B is an oxo derivative.

Mix 1-[[(4-fluorophenyl)methyl]-1H-benzimidazol-2-yl][1-(4-piperidinyl)]methanone, trifluoroacetic acid salt (5.0 g, 11.1 mmol) and pyridine (70 mL). Add, by dropwise addition, trifluoroacetyl chloride (1.62 g, 12.2 mmol) and stir overnight. Remove excess pyridine in vacuo and dissolve the residue in a two-phase mixture of ethyl acetate/water. Separate the organic phase and extract the aqueous phase with additional ethyl acetate (2×). Wash the combined organic phases with water, then with brine and dry (MgSO4). Evaporate the solvent in vacuo to give a foam. Purify by flash chromatography (10% ethyl acetate/hexane) to give the crude product as a solid. Recrystallize (cyclohexane) to give the title compound; mp 135°–37° C. This compound exhibited a pA2 value of 7.99 in the guinea pig ileum screen using the method of Van Rossum.

Anal. Calcd for $C_{22}H_{19}F_4N_3O_2$: C, 60.97; H, 4.42; N, 9.70; Found: C, 60.95; H, 4.52; N, 9.66.

A general synthetic procedure for the preparation of compounds of Formula I wherein A is either an alkyl derivative or an aralkyl derivative and B is either an amido tetrazole derivative or an alkyl tetrazole is set forth in Scheme B. In Scheme B, all substitutents, unless otherwise indicated, are as previously defined.

Scheme B

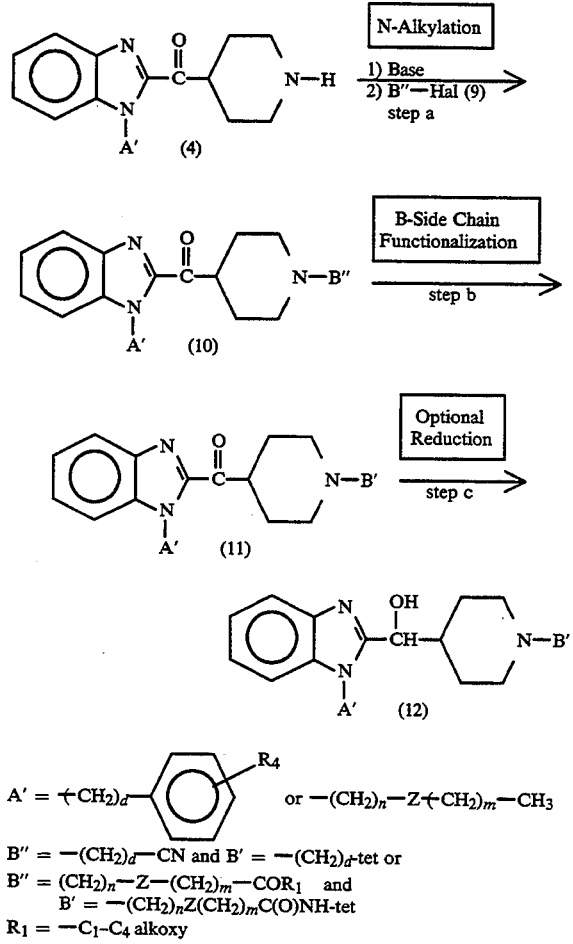

$A' = +CH_2)_d\text{—}\langle\text{phenyl-}R_4\rangle$ or $-(CH_2)_n-Z+CH_2)_m-CH_3$ $B'' = -(CH_2)_d-CN$ and $B' = -(CH_2)_d$-tet or
$B'' = (CH_2)_n-Z-(CH_2)_m-COR_1$ and
$B' = -(CH_2)_nZ(CH_2)_mC(O)NH$-tet
$R_1 = -C_1-C_4$ alkoxy In general, an apppropriate piperidinyl benzimidazole derivative of Formula I in which A is either an alkyl derivative or an aralkyl derivative and B is either an amido tetrazole derivative or an alkyl tetrazole, wherein all substituents, unless otherwise indicated, are as previously defined, can be prepared in a multi-step process.

In step a, the appropriate piperidinyl benzimidazole of structure (4) is N-alkylated under basic conditions with the appropriate alkyl halide of structure (9) to give the piperidinyl benzimidazole of structure (10). Typically, the reaction conditions and isolation techniques are as described in Scheme A, step c.

The appropriate alkyl halide of structure (9) is one which has a functionality which must be reacted further in order to produce the desired product. For example, when the desired piperidinyl benzimidazole of structure (11) is one in which the group B' is represented by an alkyl tetrazole, the appropriate piperidinyl benzimidazole of structure (4) is N-alkylated with an alkyl halide of structure (9) having the formula $Hal-(CH_2)_d-CN$. Similarly, when the desired piperidinyl benzimidazole of structure (11) is one in which the group B' is represented by an amido tetrazole derivative, the appropriate piperidinyl benzimidazole of structure (4) is N-alkylated with an alkyl halide of structure (9) having the formula $Hal-(CH_2)_n-Z-(CH_2)_m-COR_1$.

In step b, the B''-side chain of the appropriate piperidinyl benzimidazole of structure (10) is functionalized in order to produce the desired piperidinyl benzimidazole of structure (11).

For example, a nitrile functionality of the appropriate piperidinyl benzimidazole of structure (10), obtained by using an alkylating agent (9) of the formula $Hal-(CH_2)_d-CN$, is converted to a tetrazole using techniques well known in the art.

Typically, an appropriate piperidinyl benzimidazole of structure (10) containing a nitrile functionality, is contacted with a molar excess of sodium azide and a molar excess of ammonium chloride. The reactants are typically contacted in a suitable organic solvent, such as dimethylformamide. The reactants are typically stirred together for a period of time ranging from 2–24 hours and at a temperature range of room temperature to 120° C. The tetrazole product is recovered from the reaction zone by extractive methods as is known in the art and purified by chromatography.

Similarly, an ester functionality of the appropriate piperidinyl benzimidazole of structure (10), obtained by using an alkylating agent (9) of the formula $Hal-(CH_2)_n-Z-(CH_2)_m-COR_1$, wherein $R_1$ is $C_1-C_4$ alkoxy, is converted to the amido tetrazole derivative using techniques well known in the art. For example, if $R_1$ is represented by —O-t-butyl, the t-butyl ester functionality is first hydrolyzed to the carboxylic acid under acidic conditions, such as with trifluoroacetic acid. The free carboxylic acid is then activated by conversion to its imidazolide using 1,1'-carbonyldiimidazole, in a suitable aprotic solvent system, such as dimethylformamide and tetrahydrofuran. The activation reaction is typically conducted under an inert atmosphere such as argon and is stirred at room temperature for a period of time ranging form 2–5 hours. 5-Aminotetrazole is then added and the reaction is typically heated at reflux for a period of time ranging from 2–5 hours. The reaction is then concentrated to a residue, dissolved in water and treated with hydrochloric acid until a pH of 6 is obtained. The resulting amido tetrazole compound is then purified by recrystallization or chromatography as described previously. It is understood that other well known methods for converting carboxylic acids to amides may also be used, such as forming an acid chloride with thionyl chloride in a suitable aprotic solvent such as methylene chloride, followed by reaction with the 5-aminotetrazole.

In optional step c, the carbonyl functionality of the piperidinyl benzimidazole of structure (11) can be reduced to the corresponding hydroxymethylene, as described previously in Scheme A, step d, to give the piperidinyl benzimadazole of structure (12).

The starting materials for use in the general synthetic procedure outlined in Scheme B are readily available to one skilled in the art.

The following examples present typical syntheses as described by Scheme B. These examples are understood to be illustrative only and are not intended to limit the scope of the invention in any way.

EXAMPLE 9

1-[[(4-Fluorophenyl)methyl]-1H-benzimidazol-2-yl][1-(tetrazole acetamide)-4-piperidinyl]methanone The purpose of this example is to demonstrate one method for the preparation of a piperidinyl benzimidazole of Formula I wherein A is an aralkyl derivative and B is an amido tetrazole derivative.

Mix 1-[[(4-fluorophenyl)methyl]-1H-benzimidazol-2-yl][1-(carboxymethyl)-4-piperidinyl]methanone (see Example 4) (376 mg, 0.951 mmol), anhydrous dimethylformamide (7 mL) and anhydrous tetrahydrofuran (14 mL) and place under an argon atmosphere. Add 1,1'-carbonyldimidazole (162 mg, 1.00 mmol) and stir at room temperature for 2 hours. Add 5-aminotetrazole (85.7 mg, 1.01 mmol) and heat to a gentle reflux for 2 hours. Concentrate to a residue and dissolve in water (10 mL). Treat with 0.3N hydrochloric acid until pH 6 is obtained. Filter the resulting white solid and air dry overnight to give an off-white solid. Recrystallize (ethanol) to give the title compound as a white powder; mp 175°–195° C. This compound exhibited a pA2 value of 8.62 in the guinea pig ileum screen using the method of Schild.

Anal. Calcd for $C_{23}H_{23}FN_8O_2$: C, 59.73; H, 5.01; N, 24.23; Found: C, 59.80; H, 5.07; N, 24.10.

A general synthetic procedure for the preparation of compounds of Formula I in which B is either an oxo derivative, a carbonyl derivative, an alkyl derivative, an aralkyl derivative or a hydrogen and A is either an oxo derivative, an alkyl derivative or a carbonyl derivative is set forth in Scheme C. In Scheme C, all substituents, unless otherwise indicated, are as previously defined.

Scheme C

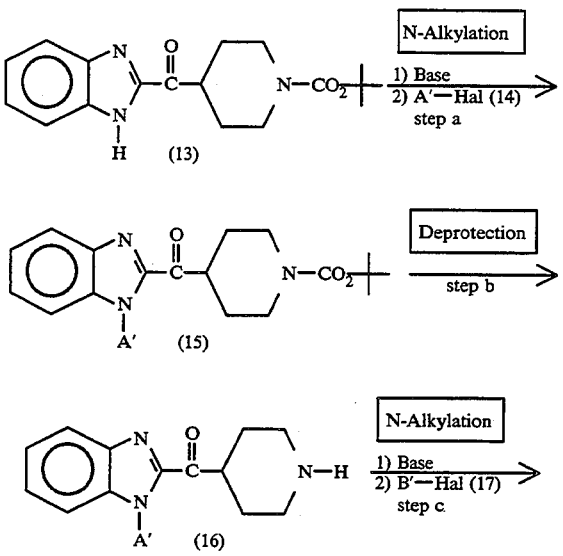

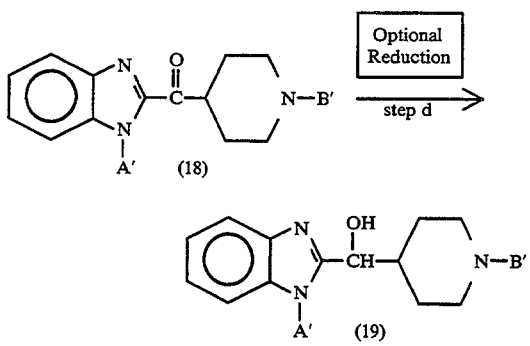

$A' = -(CH_2)_n-Z-(CH_2)_m-COR_1$ or $-C(O)R_5$ or $-(CH_2)_n-Z-(CH_2)_m-CH_3$ $B' = -(CH_2)_q-\langle\text{Ar}(R_4)\rangle$, $-(CH_2)_n-Z-(CH_2)_m-COR_1$, $-C(O)R_5$ or $-(CH_2)_n-Z-(CH_2)_m-CH_3$ $R_1 = -C_1-C_4$ alkoxy In general, an appropriate piperidinyl benzimidazole derivative of Formula I in which B is either an oxo derivative, a carbonyl derivative, an alkyl derivative, an aralkyl derivative or a hydrogen and A is either an oxo derivative, an alkyl derivative or a carbonyl derivative, wherein all substituents, unless otherwise indicated, are as previously defined, can be prepared in a multi-step process.

In step a, the benzimidazole functionality of the appropriate piperidinyl benzimidazole of structure (13) is N-alkylated under basic condition with the appropriate alkyl halide of structure (14) to give the piperidinyl benzimidazole of structure (15). Typically, reaction conditions and isolation procedures are described previously in Scheme A, step c.

In step b, the piperidine functionality of the piperidinyl benzimidazole of structure (15) is deprotected under acidic conditions to give the piperidinyl benzimidazole of structure (16) using procedures and techniques well known in the art and described in Scheme A, step b.

In step c, the piperidine functionality of the piperidinyl benzimidazole of structure (16) is N-alkylated under basic conditions with the appropriate alkyl halide of structure (17) to give the piperidinyl benzimidazole of structure (18). Typically, reaction conditions and isolation procedures are described previously in Scheme A, step c.

In optional step d, the carbonyl functionality of the piperidinyl benzimidazole of structure (18) can be reduced to the corresponding hydroxymethylene group, as described previously in Scheme A, step d, to give the piperidinyl benzimidazole of structure (19).

In addition, the compounds of Formula I, wherein A and/or B are carbonyl derivatives, the ester functionalities, wherein $R_1$ is $C_1-C_4$ alkoxy, can be converted to free carboxylic acids, wherein R1 is OH, or to amides, wherein $R_1$ is $-NR_2R_3$, or to other esters as described previously for Scheme A.

Such amides, carboxylic acids and esters of structure (18) can then be reduced to the corresponding alcohols of structure (19) by the methods described previously in optional step d.

The starting materials for use in the general synthetic procedure outlined in Scheme C are readily available to one of ordinary skill in the art. For example, piperidinyl benzimidazole derivatives of structure (13) are described in U.S. Pat. No. 4,908,372 (Mar. 13, 1990).

The following examples present typical syntheses as described by Scheme C. These examples are understood to be illustrative only and are not intended to limit the scope of the invention in any way.

EXAMPLE 10

1-[[(2-Ethoxy)ethyl]-1H-benzimidazol-2-yl][1-(carbomethoxy methoxy ethyl)-4-piperidinyl]methanone

Step a:
1-[[(2-Ethoxy)ethyl]-1H-benzimidazol-2-yl][1-(t-butyloxycarbonyl)-4-piperidinyl]methanone Mix [1H-benzimidazol-2-yl][1-(t-butyloxycarbonyl)-4-piperidinyl]methanone (4.25 g, 12.91 mmol), 2-bromoethyl ethyl ether (2.34 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO4). Evaporate the solvent in vacuo and purify by chromatography to give the title compound.

Step b:
1-[[(2-Ethoxy)ethyl]-1H-benzimidazol-2-yl][1-(4-piperidinyl)]methanone Mix 1-[[(2-ethoxy)ethyl]-1H-benzimidazol-2-yl][1-(t-butyloxycarbonyl)-4-piperidinyl]methanone (10.07 g, 26.67 mmol) and trifluoroacetic acid (75 mL). Stir at room temperature until the reaction is complete. Pour onto water and carefully neutralize with solid sodium hydrogen carbonate. Extract into ethyl acetate (2×), wash with brine and dry (MgSO4). Evaporate the solvent in vacuo and purify by chromatography to give the title compound.

Step c:
1-[[(2-Ethoxy)ethyl]-1H-benzimidazol-2-yl][1-(carbomethoxy methoxy ethyl)-4-piperidinyl]methanone Mix 1-[[(2-ethoxy)ethyl]-1H-benzimidazol-2-yl][1-(4-piperidinyl)]methanone (3.89 g, 12.91 mmol), carbomethoxy methoxy ethylbromide (3.01 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO4). Evaporate the solvent in vacuo to give and purify by chromatography to give the title compound.

EXAMPLE 11

1-[[(2-Ethoxy)ethyl]-1H-benzimidazol-2-yl][1-(carboxy methoxy ethyl)-4-piperidinyl]methanone Dissolve 1-[[(2-ethoxy)ethyl]-1H-benzimidazol-2-yl][1-(carbomethoxy methoxy ethyl)-4-piperidinyl]methanone (0.9 g, 2.15 mmol) in tetrahydrofuran/water (20 mL, 1/1). Add lithium hydroxide monohydroate (932 mg, 8.5 mmol). Seal the flask and warm to 60° C. for 3 hours. Dilute with ethyl acetate/water, acidify and separate the organic phase. Dry (MgSO4), evaporate the solvent in vacuo, and purify by ion-exchange chromatography to give the title compound.

A general synthetic procedure for the preparation of compounds of Formula I wherein A is either a carbonyl derivative or an oxo derivative and B is either an alkyl tetrazole or an amido tetrazole derivative is set forth in Scheme D. In Scheme D, all substituents, unless otherwise indicated, are as previously defined.

Scheme D

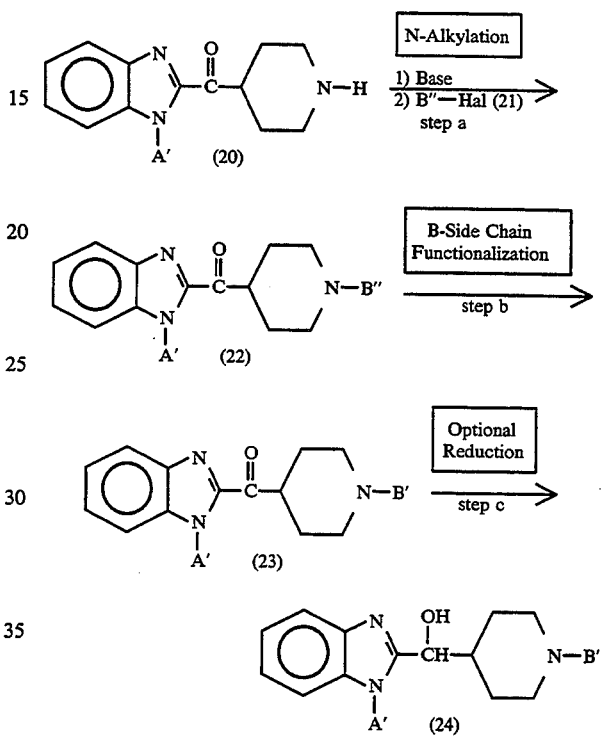

$A' = -(CH_2)_n-Z-(CH_2)_m-COR_1$ or $-C(O)R_5$
$B'' = -(CH_2)_d-CN$ and $B' = -(CH_2)_d\text{-tet}$ or
$B'' = -(CH_2)_n-Z-(CH_2)_m-COR_1$ and
$B' = -(CH_2)_nZ(CH_2)_mC(O)NHtet$
$R_1 = -C_1-C_4$ alkyoxy
$R_1' = $ t-butyloxy In general, an appropriate piperidinyl benzimidazole derivative of Formula I wherein A is either a carbonyl derivative or an oxo derivative and B is either an alkyl tetrazole or an amido tetrazole derivative, wherein all substituents, unless otherwise indicated, are as previously defined, can be prepared in a multi-step procedure.

In step a, the appropriate piperidinyl benzimidazole of structure (20) is N-alkylated under basic conditions with the appropriate alkyl halide of structure (21) to give the piperidinyl benzimidazole of structure (22). Typically, the reaction conditions and isolation techniques are as described in Scheme A, step c.

The appropriate alkyl halide of structure (21) is one which has functionality which must be reacted further in order to produce the desired product as described previously in Scheme B, step a.

In step b, the B″-side chain of the appropriate piperidinyl benzimidazole of structure (22) is functionalized in order to produce the desired piperidinyl benzimidazole of structure (23) as described previously in Scheme B, step b. It should be noted that for compounds of Formula I, wherein A' is a carbonyl derivative and B is an amido tetrazole derivative, the functionalization of the B"-side chain must necessarily include a selective deprotection of the ester functionality of the formula —$(CH_2)_n$—Z—$(CH_2)_m$—$COR_1'$ in the presence of the ester functionality of the A-side chain of the formula —$(CH_2)_n$—Z—$(CH_2)_m$—$COR_1$. For example, when $R_1'$ is t-butyloxy and $R_1$ is a $C_1$-$C_4$ alkoxy, excluding t-butyloxy, such that $R_1'$ can be selectively removed by treatment with an acid, such as trifluoracetic acid. The selection and utilization of other appropriate ester protecting groups are well known to one of ordinary skill in the art and are cited in "Protecting Groups in Organic Synthesis" by Theodora W. Greene (John Wiley and Sons 1981).

In optional step c, the carbonyl functionality of the piperidinyl benzimidazole of structure (23) can be reduced to the corresponding hydroxymethylene group, as described previously in Scheme A, step d, to give the piperidinyl benzimidazole compound of structure (24).

In addition, the compounds of Formula I, wherein A is a carbonyl derivatives, the ester functionalities, wherein $R_1$ is $C_1$-$C_4$ alkoxy, can be converted to free carboxylic acids, wherein $R_1$ is OH, or to amides, wherein $R_1$ is —$NR_2R_3$, or to other esters as described previously for Scheme A.

Such amides, carboxylic acids and esters of structure (23) can then be reduced to the corresponding alcohols of structure (24) by the methods described previously in optional step d.

The starting materials for use in the general synthetic procedure outlined in Scheme D are readily available to one skilled in the art. For example, tert-butyl 3-bromopropionate is described in *Bull. Soc. Chim. Fr.* 12, 2985-6 1984.

The following examples present typical syntheses as described by Scheme D. These examples are understood to be illustrative only and are not intended to limit the scope of the invention in any way.

EXAMPLE 12

1-[(1-Carbomethoxy methoxy ethyl)-1H-benzimidazol-2-yl][5-(tetrazolylbutyl)-4-piperidinyl]methanone Scheme C, Step a: 1-[(1-Carbomethoxy methoxy ethyl)-1H-benzimidazol-2-yl][1-(t-butyloxycarbonyl)-4-piperidinyl]methanone Mix [1H-benzimidazol-2-yl][1-(t-butyloxycarbonyl)-4-piperidinyl]methanone (4.25 g, 12.91 mmol), carbomethoxy methoxy ethylbromide (3.01 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry ($MgSO_4$). Evaporate the solvent in vacuo to give and purify by chromatography to give the title compound.

Scheme C, Step b: 1-[(1-Carbomethoxy methoxy ethyl)-1H-benzimidazol-2-yl][1-(4-piperidinyl)]methanone Mix 1-[(1-carbomethoxy methoxy ethyl)-1H-benzimidazol-2-yl][1-(t-butyloxycarbonyl)-4-piperidinyl]-methanone (11.9 g, 26.67 mmol) and trifluoroacetic acid (75 mL). Stir at room temperature until the reaction is complete. Pour onto water and carefully neutralize with solid sodium hydrogen carbonate. Extract into ethyl acetate (2×), wash with brine and dry ($MgSO_4$). Evaporate the solvent in vacuo and purify by chromatography to give the title compound.

Step a: 1-[(1-Carbomethoxy methoxy ethyl)-1H-benzimidazol-2-yl][1-(4-cyanobutyl)-4-piperidinyl]methanone Mix 1-[(1-carbomethoxy methoxy ethyl)-1H-benzimidazol-2-yl][1-(4-piperidinyl)]methanone (4.45 g, 12.91 mmol), 5-bromovaleronitrile (2.5 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry ($MgSO_4$). Evaporate the solvent in vacuo and purify by chromatography to give the title compound.

Step b: 1-[(1-Carbomethoxy methoxy ethyl)-1H-benzimidazol-2-yl][1-(5-tetrazolylbutyl)-4-piperidinyl]methanone Mix 1-[(1-carbomethoxy methoxy ethyl)-1H-benzimidazol-2-yl][1-(4-cyanobutyl)-4-piperidinyl]methanone (25.3 g, 59.4 mmol) sodium azide (3.9 g, 59.4 mmol), ammonium chloride (3.2 g, 59.4 mmol) and dimethylformamide (30 mL). Heat at 115°-120° C. for 4 hours. Cool and add another 3 equivalents of both sodium azide and ammonium chloride. Heat an additional 18 hours at 115°-120° C. Pour into water (500 mL) and extract with ethyl acetate. Separate the organic phase and wash repeatedly with water and then a brine solution. Dry ($MgSO_4$) and evaporate the solvent in vacuo. Purify by ion-exchange chromatography to give the title compound.

EXAMPLE 13

1-[(1-Carboxy methoxy ethyl)-1H-benzimidazol-2-yl][1-(4-tetrazolobutyl)-4-piperidinyl]methanone Dissolve 1-[(1-carbomethoxy methoxy ethyl)-1H-benzimidazol-2-yl][1-(4-tetrazolobutyl)-4-piperidinyl]-methanone (1.08 g, 2.15 mmol) in tetrahydrofuran/water (20 mL, 1/1). Add lithium hydroxide monohydroate (932 mg, 8.5 mmol). Seal the flask and warm to 60° C. for 3 hours. Dilute with ethyl acetate/water, acidify and separate the organic phase. Dry ($MgSO_4$), evaporate the solvent in vacuo, and purify by ion-exchange chromatography to give the title compound.

EXAMPLE 14

1-[(1-Carbomethoxy methoxy ethyl)-1H-benzimidazol-2-yl][1-[N-(5-tetrazolo)-acetamide]-4-piperidinyl]methanone Step a: 1-[(1-Carbomethoxy methoxy ethyl)-1H-benzimidazol-2-yl][1-(tert-butyl acetate)-4-piperidinyl]methanone Mix 1-[(1-carbomethoxy methoxy ethyl)-1H-benzimidazol-2-yl]-(4-piperidinyl)]methanone (4.45 g, 12.91 mmol), tert-butyl bromoacetate (2.98 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry ($MgSO_4$). Evaporate the solvent in vacuo to give and purify by chromatography to give the title compound.

Step b: 1-[(1-Carbomethoxy methoxy ethyl)-1H-benzimidazol-2-yl][1-[N-(5-tetrazole)-acetamide]-4-piperidinyl]methanone Mix 1-[(1-carbomethoxy methoxy ethyl)-1H-benzimidazol-2-yl][1-(tert-butyl acetate)-4-piperidinyl]methanone (12.24 g, 26.67 mmol) and trifluoroacetic acid (75 mL). Stir at room temperature until the reaction is complete. Pour onto water and carefully neutralize with solid sodium hydrogen carbonate. Carefully neutralize with 1N hydrochloric acid and extract into ethyl acetate (2×), wash with brine and dry (MgSO$_4$). Evaporate the solvent in vacuo and purify by chromatography to give 1-[(1-carbomethoxy methoxy ethyl)-1H-benzimidazol-2-yl][1-(carboxymethyl)-4-piperidinyl]-methanone.

Mix 1-[(1-carbomethoxy methoxy ethyl)-1H-benzimidazol-2-yl][1-(carboxymethyl)-4-piperidinyl]methanone (4.03 g, 10 mmol), 1,1'-carbonyldiimidazole (1.62 g, 10 mmol) and dimethylformamide (50 mL) under an argon atmosphere. Stir at room temperature for several hours. Add 5-amino tetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO$_4$) and evaporate the solvent in vacuo. Purify by chromatography to give the title compound.

EXAMPLE 15

1-[(1-Carboxy methoxy ethyl)-1H-benzimidazol-2-yl][1-[N-(5-tetrazole)-acetamide]-4-piperidinyl]methanone Dissolve 1-[(1-carbomethoxy methoxy ethyl)-1H-benzimidazol-2-yl][1-[N-(5-tetrazole)-acetamide]-4-piperidinyl]-methanone (0.866 mg, 2.15 mmol) in tetrahydrofuran/water (20 mL, 1/1). Add lithium hydroxide monohydroate (932 mg, 8.5 mmol). Seal the flask and warm to 60° C. for 3 hours. Dilute with ethyl acetate/water, acidify and separate the organic phase. Dry (MgSO$_4$), evaporate the solvent in vacuo, and purify by ion-exchange chromatography to give the title compound.

A general synthetic procedure for the preparation of compounds of Formula I wherein A is either an alkyl tetrazole or an amido tetrazole derivative and B is either hydrogen, an oxo derivative, a carbonyl derivative, an alkyl derivative, an aralkyl derivative or a hydrogen is set forth in Scheme E. In Scheme E, all substituents, unless otherwise indicated, are as previously defined.

Scheme E

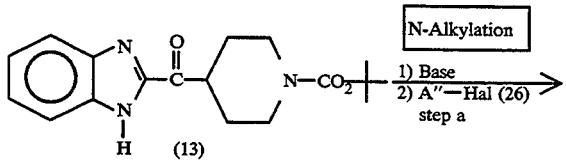

-continued
Scheme E $A'' = -(CH_2)_d-CN$ and $A' = -(CH_2)_d$-tet or
$A'' = -(CH_2)_n-Z-(CH_2)_m-COR_1$ and
$A' = -(CH_2)_n-Z-(CH_2)_m C(O)NHtet$ $B' = -(CH_2)_d$-[phenyl-R$_4$], $-(CH_2)_n-Z-(CH_2)_m-COR_1$, $-C(O)R_5$ or
$-(CH_2)_n-Z-(CH_2)_m-CH_3$
$R_1 = -C_1-C_4$ alkoxy
$R_1' = $ t-butyloxy In general, an appropriate piperidinyl benzimidazole derivative of Formula I in which A is either an alkyl tetrazole or an amido tetrazole derivative and B is either hydrogen, an oxo derivative, a carbonyl derivative, an alkyl derivative, an aralkyl derivative or a hydrogen wherein all substituents, unless otherwise indicated, are as previously defined can be prepared in a multi-step process.

In step a, the benzimidazole functionality of the appropriate piperidinyl benzimidazole of structure (13) is N-alkylated under basic conditions with the appropriate alkyl halide of structure (26) to give the piperidinyl benzimidazole of structure (27). Typically, the reaction conditions and isolation techniques are as described in Scheme A, step c.

The appropriate alkyl halide of structure (26) is one which has a functionality which must be reacted further in order to produce the desired product as described previously in Scheme B, step a.

In step b, the piperidine functionality of the piperidinyl benzimidazole of structure (27) is deprotected under acidic conditions to give the piperidinyl benzimidazole of structure (28) using procedures and techniques well known in the art and described previously in Scheme A, step b.

In step b, it may be necessary to reesterify the carboxylic acid functionality in the case where A″ is represented by —(CH$_2$)$_n$—Z—(CH$_2$)$_m$—COR$_1$′ due to the conditions of the reaction. For example, the product obtained from step b may be reacted with a large molar excess of tert-butylacetate and a molar excess of perchloric acid. Typically, the reactants are contacted at a temperature range of from 0° C.-24° C. and for a period of time ranging from 24 hours to 5 days. The product may be recovered from the reaction zone by first extracting the organic phase with aqueous hydrochloric acid, neutralizing with sodium hydrogen carbonate and then extracting with an organic solvent such as ethyl ether. The product may be purified by techniques such as chromatography.

In step c, the piperidine functionality of the appropriate piperidinyl benzimidazole of structure (28) is N-alkylated under basic conditions with the appropriate alkyl halide of structure (29) to give the piperidinyl benzimidazole of structure (30). Typically, the reaction conditions and isolation techniques are as described in Scheme A, step c.

In step d, the A″-side chain of the appropriate piperidinyl benzimidazole of structure (30) is functionalized in order to produce the desired piperidinyl benzimidazole of structure (31) as described previously in Scheme B, step b. In order to prepare compounds of Formula I wherein A is an amido tetrazole derivative and B is a carbonyl derivative, it is necessary that the ester functionality in the A″-side chain be selectively hydrolyzed in the presence of the ester functionality of the B-side chain as described previously in Scheme D, step b.

In optional step e, the carbonyl functionality of the piperidinyl benzimidazole of structure (31) can be reduced to the corresponding hydroxymethylene group, as described previously in Scheme A, step d, to give the piperidinyl benzimidazole of structure (32). For those piperidinyl benzimidazole derivatives of Formula I in which A is either an alkyl tetrazole or an amido tetrazole derivative and B is hydrogen, the A″-side chain of the appropriate piperidinyl benzimidazole of structure (27) is functionalized in order to produce an appropriate N-protected piperidinyl benzimidazole as described previously in Scheme D, step b. The piperidine functionality of the appropriate N-protected piperidinyl benzimidazole is then deprotected under acidic conditions to give the piperidinyl benzimidazole derivative of Formula I in which A either an alkyl tetrazole or an amido tetrazole derivative and B is hydrogen by using procedures and techniques well known in the art and described previously in Scheme A, step b.

In addition, the compounds of Formula I, wherein B is a carbonyl derivatives, the ester functionalities, wherein R$_1$ is C$_1$-C$_4$ alkoxy, can be converted to free carboxylic acids, wherein R$_1$ is OH, or to amides, wherein R$_1$ is —NR$_2$R$_3$, or to other esters as described previously for Scheme A.

Such amides, carboxylic acids and esters of structure (31) can then be reduced to the corresponding alcohols of structure (32) by the methods described previously in Scheme A, optional step d.

The starting materials for use in the general synthetic procedure outlined in Scheme E are readily available to one of ordinary skill in the art.

The following examples present typical syntheses as described by Scheme E. These examples are understood to be illustrative only and are not intended to limit the scope of the invention in any way.

EXAMPLE 16

1-[(4-Tetrazole butyl]-1H-benzimidazol-2-yl][1-(1-carbomethoxy methoxy ethyl)-4-piperidinyl]methanone Step a:
1-[(4-Cyanobutyl)-1H-benzimidazol-2-yl][1-(t-butyloxycarbonyl)-4-piperidinyl]methanone Mix [1H-benzimidazol-2-yl][1-(t-butyloxycarbonyl)-4-piperidinyl]methanone (4.25 g, 12.91 mmol), 5-bromovaleronitrile (2.5 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO$_4$). Evaporate the solvent in vacuo and purify by chromatography to give the title compound.

Step b:
1-[(4-Cyanobutyl)-1H-benzimidazol-2-yl][1-(4-piperidinyl)]methanone

Mix 1-[(5-cyanopentyl)-1H-benzimidazol-2-yl][1-(t-butyloxycarbonyl)-4-piperidinyl]methanone (10.9 g, 26.67 mmol) and trifluoroacetic acid (75 mL). Stir at room temperature until the reaction is complete. Pour onto water and carefully neutralize with solid sodium hydrogen carbonate. Extract into ethyl acetate (2×), wash with brine and dry (MgSO$_4$). Evaporate the solvent in vacuo and purify by chromatography to give the title compound.

Step c:
1-[(4-Cyanobutyl)-1H-benzimidazol-2-yl][1-(1-carbomethoxy methoxy ethyl)-4-piperidinyl]methanone Mix 1-[(4-cyanobutyl)-1H-benzimidazol-2-yl][1-(4-piperidinyl)]methanone (4.0 g, 12.91 mmol), carbomethoxy methoxy ethylbromide (3.0 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO$_4$). Evaporate the solvent in vacuo and purify by chromatography to give the title compound.

Step d: 1-[(4-Tetrazole butyl)-1H-benzimidazol-2-yl][1-(1-carbomethoxy methoxy ethyl)-4-piperidinyl]methanone Mix 1-[(4-cyanobutyl)-1H-benzimidazol-2-yl][1-(1-carbomethoxy methoxy ethyl)-4-piperidinyl]methanone (25.3 g, 59.4 mmol) sodium azide (3.9 g, 59.4 mmol), ammonium chloride (3.2 g, 59.4 mmol) and dimethylformamide (30 mL). Heat at 115°-120° C. for 4 hours. Cool and add another 3 equivalents of both sodium azide and ammonium chloride. Heat an additional 18 hours at 115°-120° C. Pour into water (500 mL) and extract with ethyl acetate. Separate the organic phase and wash repeatedly with water and then a brine solution. Dry (MgSO4) and evaporate the solvent in vacuo. Purify by chromatography to give the title compound.

EXAMPLE 17

1-[(4-Tetrazole butyl)-1H-benzimidazol-2-yl][1-(1-carboxy methoxy ethyl)-4-piperidinyl]methanone Dissolve 1-[(4-tetrazole butyl)-1H-benzimidazol-2-yl][1-(1-carbomethoxy methoxy ethyl)-4-piperidinyl]methanone (1.01 g, 2.15 mmol) in tetrahydrofuran/water (20 mL, 1/1). Add lithium hydroxide monohydroate (932 mg, 8.5 mmol). Seal the flask and warm to 60° C. for 3 hours. Dilute with ethyl acetate/water, acidify and separate the organic phase. Dry (MgSO4), evaporate the solvent in vacuo, and purify by ion-exchange chromatography to give the title compound.

EXAMPLE 18

1-[[N-(5-Tetrazole)-acetamide]-1H-benzimidazol-2-yl][1-(carbomethoxy methoxy ethyl)-4-piperidinyl]methanone Step a: 1-[(tert-Butyl acetate)-1H-benzimidazol-2-yl][1-(t-butyloxycarbonyl)-4-piperidinyl]methanone Mix [1H-benzimidazol-2-yl][1-(t-butyloxycarbonyl)-4-piperidinyl]methanone (4.25 g, 12.91 mmol), tert-butyl bromoacetate (2.98 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO4). Evaporate the solvent in vacuo to give and purify by chromatography to give the title compound.

Step b: 1-[(tert-Butyl acetate)-1H-benzimidazol-2-yl][(4-piperidinyl)]methanone

Mix 1-[(tert-butyl propionate)-1H-benzimidazol-2-yl][1-(tert-butyl acetate)-4-piperidinyl]methanone (12.05 g, 26.67 mmol) and trifluoroacetic acid (75 mL). Stir at room temperature until the reaction is complete. Pour onto water and carefully neutralize with solid sodium hydrogen carbonate. Extract into ethyl acetate (2×), wash with brine and dry (MgSO4). Evaporate the solvent in vacuo and purify by chromatography to give 1-[(carboxymethyl)-1H-benzimidazol-2-yl][1-(4-piperidinyl)]methanone.

Mix 1-[(carboxymethyl)-1H-benzimidazol-2-yl][1-(4-piperidinyl)]methanone (1.20 g, 4 mmol), tert-butyl acetate (60 mL). Add, over 15 minutes, perchloric acid (442 mg, 4.4 mmol). Stir for several days at room temperature. Cool to 0° C. and extract with 0.5N hydrochloric acid (4×10 mL). Neutralize with saturated sodium hydrogen carbonate and extract into ethyl ether (4×). Dry (MgSO4), evaporate the solvent in vacuo and purify by chromatography.

Step c: 1-[(tert-Butyl acetate)-1H-benzimidazol-2-yl][1-(1-carbomethoxy methoxy ethyl)-4-piperidinyl]methanone Mix 1-[(tert-butyl acetate)-1H-benzimidazol-2-yl][1-(4-piperidinyl)]methanone (4.43 g, 12.91 mmol), carbomethoxy methoxy ethylbromide (3.01 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO4). Evaporate the solvent in vacuo to give and purify by chromatography to give the title compound.

Step d: 1-[[N-(5-Tetrazole)-acetamide]-1H-benzimidazol-2-yl][1-(1-carbomethoxy methoxy ethyl)-4-piperidinyl]methanone Mix 1-[(tert-butyl acetate)-1H-benzimidazol-2-yl][1-(1-carbomethoxy methoxy ethyl)-4-piperidinyl]methanone (12.24 g, 26.67 mmol) and trifluoroacetic acid (75 mL). Stir at room temperature until the reaction is complete. Pour onto water and carefully neutralize with solid sodium hydrogen carbonate. Carefully neutralize with 1N hydrochloric acid and extract into ethyl acetate (2×), wash with brine and dry (MgSO4). Evaporate the solvent in vacuo and purify by chromatography to give 1-[(carboxymethyl)-1H-benzimidazol-2-yl][1-(1-carbomethoxy methoxy ethyl)-4-piperidinyl]methanone.

Mix 1-[(carboxymethyl)-1H-benzimidazol-2-yl][1-(1-carbomethoxy methoxy ethyl)-4-piperidinyl]methanone (4.03 g, 10 mmol), 1,1'-carbonyldiimidazole (1.62 g, 10 mmol) and dimethylformamide (50 mL) under an argon atmosphere. Stir at room temperature for several hours. Add 5-aminotetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO4) and evaporate the solvent in vacuo. Purify by chromatoraphy to give the title compound.

EXAMPLE 19

1-[[N-(5-Tetrazole)-acetamide]-1H-benzimidazol-2-yl][1-(carboxy methoxy ethyl)-4-piperidinyl]methanone Dissolve 1-[[N-(5-tetrazole)-acetamide]-1H-benzimidazol-2-yl][1-(1-carbomethoxy methoxy ethyl)-4-piperidinyl]methanone (1.01 g, 2.15 mmol) in tetrahydrofuran/water (20 mL, 1/1). Add lithium hydroxide monohydroate (932 mg, 8.5 mmol). Seal the flask and warm to 60° C. for 3 hours. Dilute with ethyl acetate/water, acidify and separate the organic phase. Dry (MgSO4), evaporate the solvent in vacuo, and purify by ion-exchange chromatography to give the title compound.

EXAMPLE 20

1-[(4-Tetrazole butyl)-1H-benzimidazol-2-yl][4-methoxyphenyl ethyl)-4-piperidinyl]methanone Step c: 1-[(4-Cyanopbutyl)-1H-benzimidazol-2-yl][1-(4-methoxyphenyl ethyl)-4-piperidinyl]methanone Mix 1-[(4-cyanobutyl)-1H-benzimidazol-2-yl][1-(4-piperidinyl)]methanone (4.0 g, 12.91 mmol), 4-methoxyphenethyl bromide (3.24 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO₄). Evaporate the solvent in vacuo and purify by chromatography to give the title compound.

Step d: 1-[(4-Tetrazole butyl)-1H-benzimidazol-2-yl][1-(4-methoxyphenyl ethyl)-4-piperidinyl]methanone Mix 1-[(4-cyanobutyl)-1H-benzimidazol-2-yl][1-(4-methoxyphenyl ethyl)-4-piperidinyl]methanone (2.64 g, 59.4 mmol), sodium azide (3.9 g, 59.4 mmol), ammonium chloride (3.2 g, 59.4 mmol) and dimethylformamide (30 mL). Heat at 115°–120° C. for 4 hours. Cool and add another 3 equivalents of both sodium azide and ammonium chloride. Heat an additional 18 hours at 115°–120° C. Pour into water (500 mL) and extract with ethyl acetate. Separate the organic phase and wash repeatedly with water and then a brine solution. Dry (MgSO₄) and evaporate the solvent in vacuo. Purify by chromatography to give the title compound.

EXAMPLE 21

1-[(4-Tetrazole butyl)-1H-benzimidazol-2-yl][1-(2-ethoxy ethyl)-4-piperidinyl]methanone

Step c: 1-[[(4-Cyanobutyl)-1H-benzimidazol-2-yl][1-(2-ethoxy ethyl)-4-piperidinyl]methanone Mix 1-[(4-cyanobutyl)-1H-benzimidazol-2-yl][1-(4-piperidinyl)]methanone (4.0 g, 12.91 mmol), 2-ethoxy ethylbromide (2.34 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO₄). Evaporate the solvent in vacuo and purify by chromatography to give the title compound.

Step d: 1-[(4-Tetrazole butyl)-1H-benzimidazol-2-yl][1-(2-ethoxy ethyl)-4-piperidinyl]methanone Mix 1-[(4-cyanobutyl)-1H-benzimidazol-2-yl][1-(2-ethoxy ethyl)-4-piperidinyl]methanone (22.7 g, 59.4 mmol) sodium azide (3.9 g, 59.4 mmol), ammonium chloride (3.2 g, 59.4 mmol) and dimethylformamide (30 mL). Heat at 115°–120° C. for 4 hours. Cool and add another 3 equivalents of both sodium azide and ammonium chloride. Heat an additional 18 hours at 115°–120° C. Pour into water (500 mL) and extract with ethyl acetate. Separate the organic phase and wash repeatedly with water and then a brine solution. Dry (MgSO₄) and evaporate the solvent in vacuo. Purify by chromatography to give the title compound.

EXAMPLE 22

1-[[N-(5-Tetrazole)-acetamide]-1H-benzimidazol-2-yl][1-(4-methoxyphenyl ethyl)-4-piperidinyl]methanone

Step c: 1-[(tert-Butyl acetate)-1H-benzimidazol-2-yl][1-(4-methoxyphenyl ethyl)-4-piperidinyl]methanone Mix 1-[(tert-butyl acetamide)-1H-benzimidazol-2-yl][1-(4-piperidinyl)]methanone (4.43 g, 12.91 mmol), 4-methoxyphenethyl bromide (3.29 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO₄). Evaporate the solvent in vacuo and purify by chromatography to give the title compound.

Step d: 1-[[N-(5-Tetrazole)-acetamide]-1H-benzimidazol-2-yl][1-(4-methoxyphenyl ethyl)-4-piperidinyl]methanone Mix 1-[(tert-butyl acetate)-1H-benzimidazol-2-yl][1-(4-methoxyphenyl ethyl)-4-piperidinyl]methanone (12.72 g, 26.67 mmol) and trifluoroacetic acid (75 mL). Stir at room temperature until the reaction is complete. Pour onto water and carefully neutralize with solid sodium hydrogen carbonate. Carefully neutralize with 1N hydrochloric acid and extract into ethyl acetate (2×), wash with brine and dry (MgSO₄). Evaporate the solvent in vacuo and purify by chromatography to give 1-[(carboxypropyl)-1H-benzimidazol-2-yl][1-(4-methoxyphenyl ethyl)-4-piperidinyl]methanone.

Mix 1-[(carboxymethyl)-1H-benzimidazol-2-yl][1-(4-methoxyphenyl ethyl)-4-piperidinyl]methanone (4.33 g, 10 mmol), 1,1'-carbonyldiimidazole (1.62 g, 10 mmol) and dimethylformamide (50 mL) under an argon atmosphere. Stir at room temperature for several hours. Add 5-aminotetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO₄) and evaporate the solvent in vacuo. Purify by chromatoaphy to give the title compound.

EXAMPLE 23

1-[[N-(5-Tetrazole)-propionamide]-1H-benzimidazol-2-yl][1-(2-ethoxy ethyl)-4-piperidinyl]methanone

Step c: 1-[(tert-Butyl acetate)-1H-benzimidazol-2-yl][1-(2-ethoxy ethyl)-4-piperidinyl]methanone Mix 1-[(tert-butyl acetate)-1H-benzimidazol-2-yl][1-(4-piperidinyl)]methanone (4.43 g, 12.91 mmol), 2-ethoxy ethylbromide (2.34 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO₄). Evaporate the solvent in vacuo and purify by chromatography to give the title compound.

Step d: 1-[[N-(5-Tetrazole)-acetamide]-1H-benzimidazol-2-yl][1-(2-ethoxy ethyl)-4-piperidinyl]methanone Mix 1-[(tert-butyl acetate)-1H-benzimidazol-2-yl][1-(2-ethoxy ethyl)-4-piperidinyl]methanone (11.07 g, 26.67 mmol) and trifluoroacetic acid (75 mL). Stir at room temperature until the reaction is complete. Pour onto water and carefully neutralize with solid sodium hydrogen carbonate. Carefully neutralize with 1N hydrochloric acid and extract into ethyl acetate (2×), wash with brine and dry (MgSO₄). Evaporate the solvent in vacuo and purify by chromatography to give 1-[(carboxymethyl)-1H-benzimidazol-2-yl][1-(2-ethoxy ethyl)-4-piperidinyl]methanone.

Mix 1-[(carboxymethyl)-1H-benzimidazol-2-yl][1-(2-ethoxy ethyl)-4-piperidinyl]methanone (3.59 g, 10 mmol), 1,1'-carbonyldiimidazole (1.62 g, 10 mmol) and dimethylformamide (50 mL) under an argon atmosphere. Stir at room temperature for several hours. Add 5-amino tetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO$_4$) and evaporate the solvent in vacuo. Purify by chromatoaphy to give the title compound.

A general synthetic procedure for the preparation of compounds of Formula I wherein A is either an alkyl tetrazole or an amido tetrazole derivative and B is either an alkyl tetrazole or an amido tetrazole derivative is set forth in Scheme F. In Scheme F, all substituents, unless otherwise indicated, are as previously defined.

in order to produce the desired product as described previously in Scheme B, step a.

In step b$_1$, the A"-side chain of the appropriate piperidinyl benzimidazole of structure (35) is functionalized in order to produce the desired piperidinyl benzimidazole of structure (36) as described previously in Scheme B, step b.

Similarly, in step b$_2$, the B"-side chain of the appropriate piperidinyl benzimidazole of structure (35) is functionalized in order to produce the desired piperidinyl benzimidazole of structure (37) as described previously in Scheme B, step b.

In step c$_1$, the B"-side chain of the appropriate

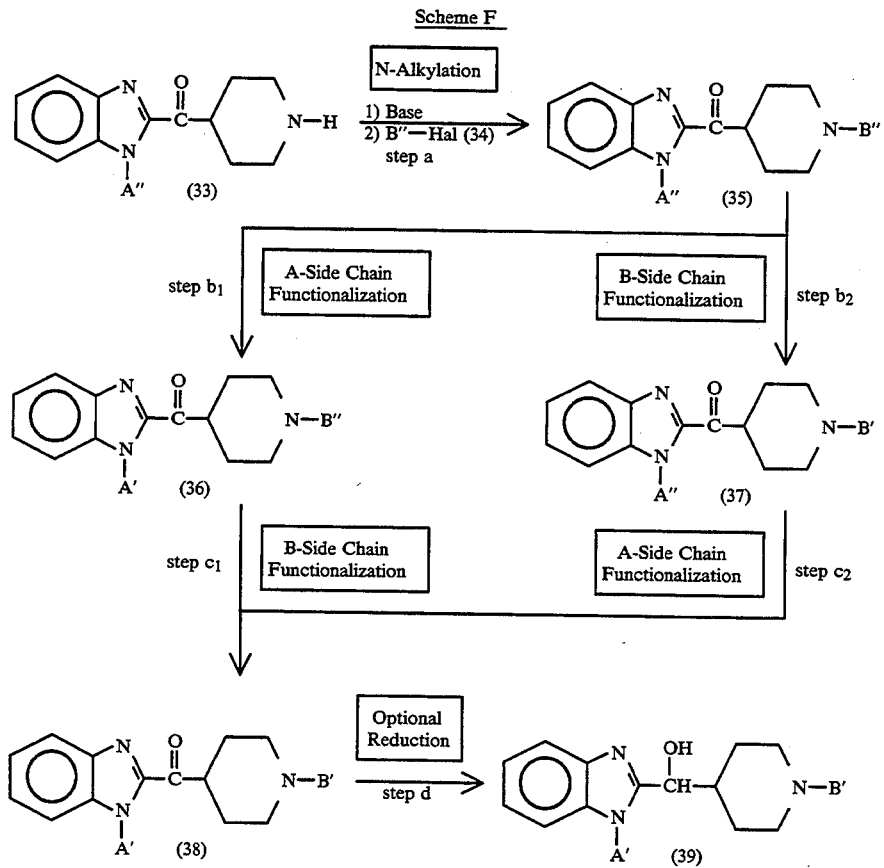

Scheme F

A" = —(CH$_2$)$_d$—CN and A' = —(CH$_2$)$_d$-tet or
A" = —(CH$_2$)$_n$—Z—(CH$_2$)$_m$—COR$_1$' and
A' = —(CH$_2$)$_n$—Z—(CH$_2$)$_m$—C(O)—NHtet
B" = —(CH$_2$)$_d$—CN and B' = —(CH$_2$)$_d$-tet or
B" = —(CH$_2$)$_n$—Z—(CH$_2$)$_m$—COR$_1$' and
B' = —(CH$_2$)$_n$—Z—(CH$_2$)$_m$—C(O)NHtet
R$_1$ = —C$_1$-C$_4$ alkoxy In general, an appropriate piperidinyl benzimidazole derivative of Formula I in which A is either an alkyl tetrazole or an amido tetrazole derivative and B is either an alkyl tetrazole or an amido tetrazole derivative can be prepared in a multi-step process.

In step a, the piperidine functionality of the appropriate piperidinyl benzimidazole of structure (33) is N-alkylated under basic conditions with the appropriate alkyl halide of structure (34) to give the piperidinyl benzimidazole of structure (35). Typically, the reaction conditions and isolation techniques are as described in Scheme A, step c.

The appropriate alkyl halide of structure (34) is one which has functionality which must be reacted further piperidinyl benzimidazole of structure (36) is functionalized in order to produce the desired piperidinyl benzimidazole of structure (38) as described previously in Scheme B, step b.

Similarly, in step c$_2$, the A"-side chain of the appropriate piperidinyl benzimidazole of structure (37) is functionalized in order to produce the desired piperidinyl benzimidazole of structure (38) as described previously in Scheme B, step b.

In optional step d, the carbonyl functionality of the piperidinyl benzimidazole of structure (38) can be reduced to the corresponding hydroxymethylene group, as described previously in Scheme A, step d, to give the piperidinyl benzimidazole of structure (39).

The starting materials for use in the general synthetic procedure outlined in Scheme F are readily available to one skilled in the art.

The following examples present typical syntheses as described by Scheme F. These examples are understood to be illustrative only and are not intended to limit the scope of the invention in any way.

EXAMPLE 24

1-[(4-Tetrazole butyl)-1H-benzimidazol-2-yl][1-(4-tetrazole butyl)-4-piperidinyl]methanone Step a: 1-[(4-Cyanobutyl)-1H-benzimidazol-2-yl][1-(4-cyanobutyl)-4-piperidinyl]methanone Mix 1-[(4-cyanobutyl)-1H-benzimidazol-2-yl][1-(4-piperidinyl)]methanone (4.0 g, 12.91 mmol), 5-bromovaleronitrile (2.5 g, 15.3 mmol), potassium carbonate (5.29 g, 38.25 mmol) and dimethylformamide (100 mL). Stir and heat at 90° C. overnight. Allow to cool to room temperature, dilute with water and extract with ethyl acetate (2×). Wash the combined organic phases with water (3×), then brine and dry (MgSO$_4$). Evaporate the solvent in vacuo and purify by chromatography to give the title compound.

Step b and Step c: 1-[(4-Tetrazole butyl)-1H-benzimidazol-2-yl][1-(4-tetrazole butyl)-4-piperidinyl]methanone Mix 1-[(4-cyanobutyl)-1H-benzimidazol-2-yl][1-(4-cyanobutyl)-4-piperidinyl]methanone (12.1 g, 29.7 mmol) sodium azide (3.9 g, 59.4 mmol), ammonium chloride (3.2 g, 59.4 mmol) and dimethylformamide (50 mL). Heat at 115°–120° C. for 4 hours. Cool and add another 3 equivalents of both sodium azide and ammonium chloride. Heat an additional 18 hours at 115°–120° C. Pour into water (500 mL) and extract with ethyl acetate. Separate the organic phase and wash repeatedly with water and then a brine solution. Dry (MgSO$_4$) and evaporate the solvent in vacuo. Purify by chromatography to give the title compound.

EXAMPLE 25

1-[(4-Tetrazole butyl)-1H-benzimidazol-2-yl][1-[N-(5-tetrazole)-acetamide]-4-piperidinyl]methanone Step a: 1-[(4-Cyanobutyl)-1H-benzimidazol-2-yl][1-(tert-butyl acetate)-4-piperidinyl]methanone Mix 1-[(4-cyanobutyl)-1H-benzimidazol-2-yl][1-(4-piperidinyl)]methanone (4.0 g, 12.91 mmol), tert-butyl acetate (2.98 g, 15.3 mmol), potassium carbonate (5.29 g, 38.25 mmol) and dimethylformamide (100 mL ). Stir and heat and at 90° C. overnight. Allow to cool to room temperature, dilute with water and extract with ethyl acetate (2×). Wash the combined organic phases with water (3×), then brine and dry (MgSO$_4$). Evaporate the solvent in vacuo and purify by chromatography to give the title compound.

Step b$_2$: 1-[(4-Cyanobutyl)-1H-benzimidazol-2-yl][1-[N-(5-tetrazole)-acetamide]-4-piperidinyl]methanone Mix 1-[(4-cyanobutyl)-1H-benzimidazol-2-yl][1-(tert-butyl acetate)-4-piperidinyl]methanone (11.31 g, 26.67 mmol) and trifluoroacetic acid (75 mL). Stir at room temperature until the reaction is complete. Pour onto water and carefully neutralize with solid sodium hydrogen carbonate. Extract into ethyl acetate (2×), wash with brine and dry (MgSO$_4$). Evaporate the solvent in vacuo and purify by chromatography to give 1-[(4-cyanobutyl)-1H-benzimidazol-2-yl][1-(carboxymethyl)-4-piperidinyl]methanone.

Mix 1-[(4-cyanobutyl)-1H-benzimidazol-2-yl][1-(carboxymethyl)-4-piperidinyl]methanone (3.68 g, 10 mmol), 1,1'-carbonyldiimidazole (1.62 g, 10 mmol) and dimethylformamide (50 mL) under an argon atmosphere. Stir at room temperature for several hours. Add 5-amino tetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO$_4$) and evaporate the solvent in vacuo. Purify by chromatography to give the title compound.

Step c$_2$: 1-[(4-Tetrazole butyl)-1H-benzimidazol-2-yl][N-(5-tetrazole)-aacetamide)-4-piperidinyl]methanone Mix 1-[(4-cyanobutyl)-1H-benzimidazol-2-yl][1-[N-(5-tetrazole)-acetamide]-4-piperidinyl]methanone (25.8 g, 59.4 mmol) sodium azide (3.9 g, 59.4 mmol), ammonium chloride (3.2 g, 59.4 mmol) and dimethylformamide (30 mL). Heat at 115°–120° C. for 4 hours. Cool and add another 3 equivalents of both sodium azide and ammonium chloride. Heat an additional 18 hours at 115°–120° C. Pour into water (500 mL) and extract with ethyl acetate. Separate the organic phase and wash repeatedly with water and then a brine solution. Dry (MgSO$_4$) and evaporate the solvent in vacuo. Purify by chromatography to give the title compound.

EXAMPLE 26

1-[[N-(5-Tetrazole)-acetamide]-1H-benzimidazol-2-yl][1-(4-tetrazole butyl)-4-piperidinyl]methanone Step a: 1-[(tert-Butyl acetate)-1H-benzimidazol-2-yl][1-(4-cyanobutyl)-4-piperidinyl]methanone Mix 1-[(tert-butyl acetate)-1H-benzimidazol-2-yl][1-(4-piperidinyl)]methanone (4.27 g, 12.91 mmol), 5-bromo valeronitrile (2.5 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO$_4$). Evaporate the solvent in vacuo and purify by chromatography to give the title compound.

Step b$_1$: 1-[[N-(5-Tetrazole)-acetamide]-1H-benzimidazol-2-yl][1-(4-cyanobutyl)-4-piperidinyl]methanone Mix 1-[(tert-butyl acetate)-1H-benzimidazol-2-yl][1-(4-cyanobutyl)-4-piperidinyl]methanone (11.31 g, 26.67 mmol) and trifluoroacetic acid (75 mL). Stir at room temperature until the reaction is complete. Pour onto water and carefully neutralize with solid sodium hydrogen carbonate. Carefully neutralize with 1N hydrochloric acid and extract into ethyl acetate (2×), wash with brine and dry (MgSO$_4$). Evaporate the solvent in vacuo and purify by chromatography to give 1-[(carboxymethyl)-1H-benzimidazol-2-yl][1-(4-cyanobutyl)-4-piperidinyl]methanone.

Mix 1-[(carboxymethyl)-1H-benzimidazol-2-yl][1-(4-cyanobutyl)-4-piperidinyl]methanone (3.68 g, 10 mmol), 1,1'-carbonyldiimidazole (1.62 g, 10 mmol) and dimethylformamide (50 mL) under an argon atmosphere. Stir at room temperature for several hours. Add 5-aminotetrazole monohydrate (1.03 g, 10 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO4) and evaporate the solvent in vacuo. Purify by chromatoaphy to give the title compound.

Step c$_1$:
1-[[N-(5-Tetrazole)-acetamide]-1H-benzimidazol-2-yl][1-(4-tetrazole butyl)-4-piperidinyl]methanone Mix 1-[[N-(5-tetrazole)-acetamide]-1H-benzimidazol-2-yl][1-(4-cyanobutyl)-4-piperidinyl]methanone (25.8 g, 59.4 mmol) sodium azide (3.9 g, 59.4 mmol), ammonium chloride (3.2 g 59.4 mmol) and dimethylformamide (30 mL). Heat at 115°–120° C. for 4 hours. Cool and add an other 3 equivalents of both sodium azide and ammonium chloride. Heat an additional 18 hours at 115°–120° C. Pour into water (500 mL) and extract with ethyl acetate. Separate the organic phase and wash repeatedly with water and then a brine solution. Dry (MgSO4) and evaporate the solvent in vacuo. Purify by chromatography to give the title compound.

EXAMPLE 27

1-[[N-(5-Tetrazole)-acetamide]-1H-benzimidazol-2-yl][1-[N-(5-tetrazole)-acetamide]-4-piperidinyl]methanone Step a: 1-[(tert-Butyl acetate)-1H-benzimidazol-2-yl][1-(tert-butyl acetate)-4-piperidinyl]methanone Mix 1-[(tert-butyl acetate)-1H-benzimidazol-2-yl][1-(4-piperidinyl)]methanone (4.42 g, 12.91 mmol), tert-butyl acetate (2.98 g, 15.3 mmol), potassium carbonate (5.29 g, 38.25 mmol) and dimethylformamide (100 mL). Stir and heat and at 90° C. overnight. Allow to cool to room temperature, dilute with water and extract with ethyl acetate (2×). Wash the combined organic phases with water (3×), then brine and dry (MgSO4). Evaporate the solvent in vacuo and purify by chromatography to give the title compound.

Step b amd Step c:
1-[[N-(5-Tetrazole)-acetamide]-1H-benzimidazol-2-yl][1-[N-(5-tetrazole)-acetamide]-4-piperidinyl]methanone Mix 1-[(tert-butyl acetate)-1H-benzimidazol-2-yl][1-(tert-butyl acetate)-4-piperidinyl]methanone (12.19 g, 26.67 mmol) and trifluoroacetic acid (75 mL). Stir at room temperature until the reaction is complete. Pour onto water and carefully neutralize with solid sodium hydrogen carbonate. Neutralize with 1N hydrochloric acid and extract into ethyl acetate (2×), wash with brine and dry (MgSO4). Evaporate the solvent in vacuo and purify by chromatography to give 1-[(carboxymethyl)-1H-benzimidazol-2-yl][1-(carboxymethyl)-4-piperidinyl]-methanone.

Mix 1-[(carboxymethyl)-1H-benzimidazol-2-yl][1-(carboxymethyl)-4-piperidinyl]methanone (3.45 g, 10 mmol), 1,1'-carbonyldiimidazole (3.24 g, 20 mmol) and dimethylformamide (750 mL) under an argon atmosphere. Stir at room temperature for several hours. Add 5-aminotetrazole monohydrate (2.06 g, 20 mmol) and heat at reflux for several hours. Evaporate the solvent in vacuo and dissolve the residue in water. Treat with hydrochloric acid until the solution is pH 6. Extract into ethyl acetate (3×) and separate the organic phase. Dry (MgSO4) and evaporate the solvent in vacuo. Purify by chromatoraphy to give the title compound.

An alternative method for preparing the compounds of Formula I wherein A is either an alkyl derivative or an aralkyl derivative and B is either an alkyl derivative or an aralkyl derivative is set forth in Scheme G. In Scheme G, all substituents are as previously defined unless otherwise indicated.

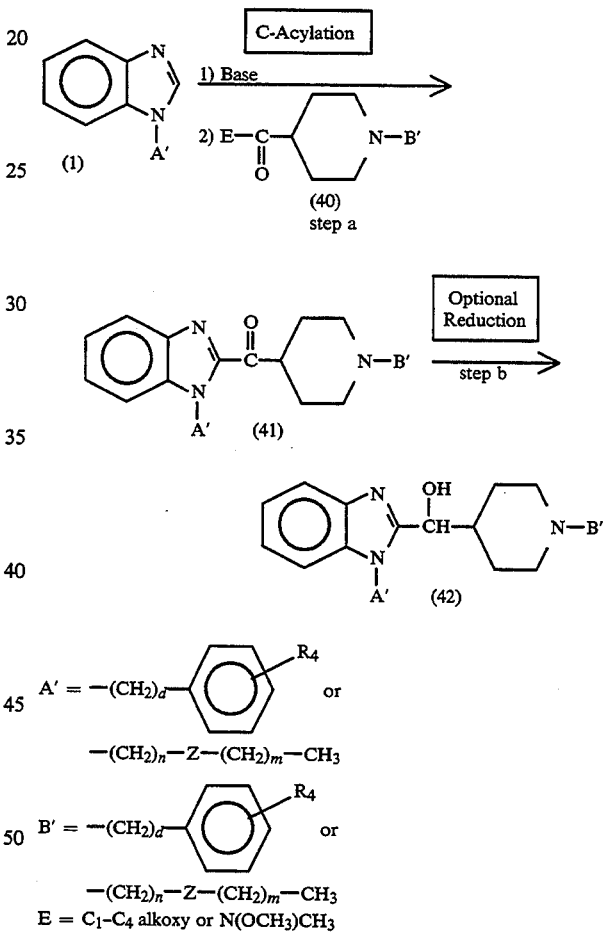

Scheme G provides an alternative general procedure for preparing the compounds of Formula I wherein A is either an alkyl derivative or an aralkyl derivative and B is either an alkyl derivative or an aralkyl derivative.

In step a, the appropriate N-alklylated benzimidazole of structure (1) is acylated with the piperidinyl derivative of structure (40) under basic conditions to give the piperidinyl benzimidazole derivative of structure (41) as described previously in Scheme A, step a.

In optional step b, the carbonyl functionality of the piperidinyl benzimidazole of structure (41) can be reduced to the corresponding hydroxymethylene group as described previously in Scheme A, optional step d.

The starting materials for use in the general synthetic procedure outlined in Scheme G are readily available to one of ordinary skill in the art.

The following examples present typical syntheses as described by Scheme G. These examples are understood to be illustrative only and are not intended to limit the scope of the invention in any way.

EXAMPLE 28

1[[(4-Fluorophenyl)methyl]-1H-benzimidazol-2-yl][1-methyl-4-piperidinyl]methanone The purpose of this example is to demonstrate an alternative preparation of a piperidinyl benzimidazole of Formula I wherein Y is represented by CO, A is an aralkyl derivative and B is an alkyl derivative.

Dissolve isonipecotic acid methyl ester, hydrochloride (43.7 g, 243 mmol) in a minimum amount of water. Add potassium bicarbonate (24.3 g, 243 mmol) and warm the solution on a steam bath for 20 minutes. Evaporate the water in vacuo, treat the residue with methanol and filter. Evaporate the filtrate in vacuo to give isonipecotic acid methyl ester as a oily yellow solid.

Dissolve isonipecotic acid methyl ester in formaldehyde (19.4 mL of a 37.5% solution in water, 262 mmol) and treat with formic acid (10.2 mL of a 90% solution, 240 mmol). Heat on a steam bath for 2 hours and evaporate the solvent in vacuo. Dissolve the residue in ethyl ether, dry ($MgSO_4$), filter and evaporate the filtrate in vacuo. Purify by distillation under an argon atmosphere to give 1-methyl-4-piperidinecarboxylic acid, methyl ester as a clear colorless oil (bp 195°–205° C., 760 mm).

Dissolve 1-[(4-fluorophenyl)methyl]-1H-benzimidazole (7.64 g, 36.0 mmol) in anhydrous tetrahydrofuran (25 mL), place under an argon atmosphere and cool to −78° C. Add, by slow addition, n-butyllithium (15.4 mL of a 2.5M solution in hexane, 38.5 mmol) and stir for 15 minutes. Add, by dropwise addition, a solution of 1-methyl-4-piperidinecarboxylic acid, methyl ester (5.66 g, 36.0 mmol) in anhydrous tetrahydrofuran (25 mL) and stir at −78° C. for 5 minutes. Remove the ice bath and stir for an additional 15 minutes. Quench with water, separate the organic phase and extract the aqueous phase with ethyl ether. Combine the organic phases, wash with saturated aqueous sodium chloride and dry ($MgSO_4$). Filter and evaporate the solvent in vacuo. Purify by silica gel chromatography (acetone) and crystallize (hexane) to give the title compound as an off-white crystalline solid; mp 121°–122° C. This compound exhibited a pA2 value of 9.18 in the guinea pig ileum screen described on pages 66 and 67 of this application using the method of Schild.

EXAMPLE 29

1-[[(4-Fluorophenyl)methyl]-1H-benzimidazol-2-yl][1-methyl-4-piperidinyl]methanol The purpose of this example is to demonstrate an alternative preparation of a piperidinyl benzimidazole of Formula I wherein Y is represented by CHOH, A is an aralkyl derivative and B is an alkyl derivative.

Dissolve 1-[[(4-fluorophenyl)methyl]-1H-benzimidazol-2-yl][1-methyl-4-piperidinyl]methanone (4.2 g, 12.0 mmol) in methanol (50 mL) and cool to 0° C. Add sodium borohydride (3.3 g, 87.3 mmol) in six equal portions over a period of 6 hours. Add water and evaporate the methanol in vacuo. Extract the resulting aqueous suspension with methylene chloride and dry ($MgSO_4$). Filter, evaporate the solvent in vacuo and purify by silica gel chromatography (methanol) to give a white residue. Dissolve the residue in methylene chloride, partition between water and methylene chloride and separate the organic phase. Wash the organic phase with saturated sodium chloride and dry ($MgSO_4$). Filter, evaporate the solvent in vacuo and crystallize (1:1 cyclohexane:hexane) to give the title compound as white crystals; mp 84°–85° C. This compound exhibited a pA2 value of 8.63 in the guinea pig ileum screen described on pages 66 and 67 of this application. The value was caculated by the method of Schild.

As noted above, the compounds of Formula I are useful in the treatment of allergic diseases. They are $H_1$ antagonists. They also inhibit the release of histamine, leukotrienes, PAF, and other autocoids from sensitized mast cells (i.e. the compounds exhibit a cromolyn like efffect). The compounds can be used to either terminate an allergic response that has already been initiated or the compounds can be used prophylatically to prevent the occurence of an allergic reaction.

One method of demonstrating the compounds utility as antihistamines is the following test protocol. One group of 10 guinea pigs is dosed orally with from about 0.1 mg/kg to about 100 mg/kg of the test compound. A control group of 10 guinea pigs is dosed orally with a similar volume of vehicle (a solution of 0.5% methylcellulose and 1% ethanol). Both groups should be anesthetized and their dorsal areas shaved. One hour later, both groups are given intravenous injections of 1% Evans Blue Dye (1 ml) via the jugular vein. Immediately following the dye injection, both groups are injected intradermally in the dorsal area with histamine diphosphate injections (1 $\mu$g/0.1 ml) to produce histamine wheals. Twenty minutes after injection of the histamine, the animals are sacrificed and the size of the wheal area is then calculated from the diameter of the exposed wheal. A compound is considered to possess antihistamine activity if the wheal area of the drug treated group is statistically smaller than that of the control group.

Another method of demonstrating the antihistaminic activity of these compounds is the following protocol. It is based upon the phenomenon that histamine causes the contraction of guinea pig ileum. Antihistamine blocks this contraction. This test may be performed in the following manner:

Strips of guinea pig ileum, 2 cm in length, were set up in an isolated organ bath in tyrode's solution which had the following composition in nM (NaCl, 136.89; KCl, 2.68; $CaCl_2$, 1.8; $MgCl_2$, 1.05; $NaH_2PO_4$, 0.42; $NaHCO_3$, of the tissue were measured isotonically (Grass FTO3C transducer coupled with silver springs) under one gram resting tension and recorded in a Grass polygraph recorder. Cumulative histamine dose response experiments were then performed before and after treatment of tissues with test compounds (20 minutes incubation). Dose ratios were determined graphically at $ED_{50}$ response levels from the histamine dose response curves, and Schild plots (Arunlakshana, O. and Schild, H. O. Some quantitative uses of drug antagonists. *Br. J. Pharmacol. Chemother.* 14: 48–58, 1959) were constructed to determine the pA2 values using inverse regression line analysis (Finney, D. J. Statistical methods in biological assays. Hafner Press, New York, 1964). The pA2 is defined as the negative logarithm of the molar concentratrion of antagonist which would increase the ED50 value by 2. In some experiments, pA2 values were estimated according to the method described by van Rossum (Van Rossum, J. M., Cumulative dose-response curves: Technique for the making of dose-response curves in isolated organs and the evaluation of drug parameters. *Arch. Int. Pharmacodyn. Ther.* 143: 299-330, 1963) which uses the following relationship: $pA_2 = -\log([B]/(\text{dose ratio}-1))$, where [B] refers to the molar concentration of antagonists used. The test compounds were prepared in ethanol (0.1% v/v).

The ability of the compounds to antagonize the physiological effects of PAF (platelet activating factor) can be demonstrated by the following procedure. It is based upon the fact that PAF causes the contraction of smooth muscles such as *Taenia coli*. PAF antagonists inhibit or decrease this rate of contraction. *Taenia coli*, obtained from guinea pigs, was set up in organ bath for measurement of isotonic contractility as described above. Acetylchloine ($10^{-5}$M) was injected into the bath to produce a contractile effect which was used as a reference standard. The tissues were incubated with either vehicle or test compounds ($10^{-7}$M) for 30 minutes before they were challenged with PAF ($10^{-7}$M). The response produced by PAF in drug treated tissues were expressed as percent of that of the vehicle treated tissues after correction with the reference acetylcholine response.

The compounds are useful in the treatment of a variety allergic diseases. Examples of allergic diseases amenable to treatment with the compounds of Formula I include allergic rhinitis, seasonal rhinitis, allergic dermatoses such as acute urticaria, atopic dermatitis, and contact dermatitis. Other examples include gastrointestinal allergies which can be caused by the ingestion of either food or drugs. The compounds can also be used in the treatment of allergic pulmonary disease such as, for example, allergic asthma. Opthalmic allergies also respond to the compounds of Formula I.

The dosage range (an antihistaminic amount) at which these compounds exhibit their antihistaminic effect can vary widely depending upon the particular allergic disease being treated, the severity of the patient's disease, the patient, the particular compound being administered, the route of administration, and the presence of other underlying disease states within the patient, etc. Typically the compounds exhibit their antihistaminic effect at a dosage range of from about 0.01 mg/kg/day to about 120 mg/kg/day. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, or introperitoneally). The compounds can be introduced directly into the respiratory tract by methods such as inhalation therapy, nasal sprays, nasal drops, etc. Topical preparations of the compounds can be applied directly to the skin or opthalmic tissues.

Pharmaceutical compositions can be manufactured utilizing techniques known in the art. Typically an antihistaminic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

For nasal administration, the compounds may be dissolved in a physiologically acceptable pharmaceutical carrier and administered as a solution. Illustrative of suitable pharmaceutical carriers are water, saline, and aqueous alcoholic solutions. The pharmaceutical carrier may also contain preservatives, buffers, etc., as are known in the art.

For topical administration, the compounds can incorporated into a suitable topical carrier using techniques well known in the art. Examples of suitable topical carriers include oleaginous bases such as white petrolatum, absorption bases such as hydrophilic petrolatum, emulsion bases such as lanolin, and water soluble bases such as polyethylene glycol ointment. The topical carrier may also contain preservatives, buffers, etc., as are known in the art.

Topical administration may also be accomplished using a patch either of the reservoir and porous membrane type or of a solid matrix variety. Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces.

For inhalation therapy, the compounds can be incorporated into an aqueous alcoholic solution containing a fluorinated hydrocarbon propellant and packaged into a suitable administration device as known in the art.

As used in this application:
a) the term patient refers to warm blooded animals such as, for example, guinea pigs, mice, rats, cats, rabbits, dogs, monkeys, chimpanzees, and humans;
b) the term allergic disease refers to a condition in which the effect of histamine on the $H_1$ receptor has an adverse effect upon the patient, or in which an antigen-antibody reaction hs an adverse effect upon the patient, and,
c) the term treat refers to the ability of the compound to either relieve or alleviate the patient's disease.

What is claimed is:
1. A compound of the formula:

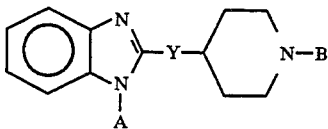

in which Y is represented by CO or CHOH; A and B are each independently represented by a substituent selected from the group consisting of:

a) a carbonyl derivative of the formula —(CH$_2$)$_n$—Z—(CH$_2$)$_m$COR$_1$ in which n and m are each independently represented by an integer from 0–3, Z is represented by a bond, O, or S and R$_1$ is represented by OH, a C$_1$–C$_4$ alkoxy or —NR$_2$R$_3$ wherein R$_2$ and R$_3$ are each independently represented by H or C$_1$–C$_4$ alkyl; and b) an amido tetrazole derivative of the formula:

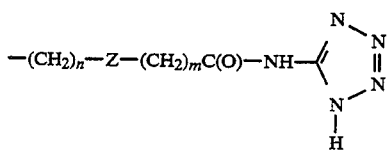

wherein n, m and Z are as previously defined; and c) an alkyl derivative of the formula —(CH$_2$)$_n$—Z—(CH$_2$)$_m$CH$_3$ wherein n, m and z are as previously defined; and d) an alkyl tetrazole of the formula:

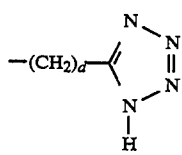

in which d is represented by an integer from 1–5; and e) an aralkyl derivative of the formula:

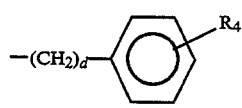

in which R$_4$ is represented by a substituent selected from the group consisting of H, C$_1$–C$_4$ alkyl, C$_1$–C$_4$ alkoxy, OH, halogen, and —CF$_3$, and d is as previously defined; and f) an oxo derivative of the formula: —C(O)R$_5$, in which R$_5$ is represented by a C$_1$–C$_4$ alkyl, C$_1$–C$_4$ alkoxy, or —NR$_2$R$_3$, wherein R$_2$ and R$_3$ are as previously defined, and the pharmaceutically acceptable salts thereof, with the proviso's: 1) that A and B are not both simultaneously aralkyl, 2) that when B is an oxo derivative in which R$_5$ is C$_1$–C$_4$ alkoxy, then A is not aralkyl, and 3) when A and/or B is a carbonyl derivative in which Z is a bond, then the sum of m and n is at least one.

2. A compound according to claim 1 in which Y is CO.

3. A compound according to claim 1 in which Y is CHOH.

4. A compound according to claim 1 in which A is an alkyl tetrazole.

5. A compound according to claim 1 in which A is an amido tetrazole derivative.

6. A compound according to claim 1 in which A is a carbonyl derivative.

7. A compound according to claim 1 in which A is an aralkyl derivative.

8. A compound according to claim 1 in which A is an oxo derivative.

9. A compound according to claim 1 in which A is an alkyl derivative.

10. A compound according to any one of claims 4, 5, 6, 7, 8 or 9 in which B is an alkyl derivative.

11. A compound according to any of claims 4, 5, 6, 7, 8, or 9 in which B is an alkyl tetrazole.

12. A compound according to any of claims 4, 5, 6, 7, 8, or 9 in which B is an amido tetrazole derivative.

13. A compound according to any of claims 4, 5, 6, 7, 8, or 9 in which B is a carbonyl derivative.

14. A compound according to any of claims 4, 5, 6, 8, or 9 in which B is an aralkyl derivative.

15. A compound according to any of claims 4, 5, 6, 7 8, or 9 in which B is an oxo derivative.

16. A compound according to claim 1 in which said compound is 1-[[(2-ethoxy)ethyl]-1H-benzimidazol-2-yl][1-[2-(4-methoxyphenyl)ethyl]-4-piperidinyl]methanone.

17. A compound according to claim 1 in which said compound is 1-[[(4-fluorophenyl)methyl]-1H-benzimidazol-2-yl][1-(carbomethoxy methoxyethyl)-4-piperidinyl]methanone.

18. A compound according to claim 1 in which said compound is 1-[[(4-fluorophenyl)methyl]-1H-benzimidazol-2-yl][1-carbo-t-butoxymethyl)-4-piperidinyl]methanone.

19. A compound according to claim 1 in which said compound is 1-[[(4-fluorophenyl)methyl]-1H-benzimidazol-2-yl][1-(carboxymethyl)-4-piperidinyl]methanone.

20. A compound according to claim 1 in which said compound is 1-[[(4-fluorophenyl)methyl]-1H-benzimidazol-2-yl][1-(N,N-diethylcarbamoyl)-4-piperidinyl]methanone.

21. A compound according to claim 1 in which said compound is 1-[[(4-fluorophenyl)methyl]-1H-benzimidazol-2-yl][1-(acetyl)-4-piperidinyl]methanone.

22. A compound according to claim 1 in which said compound is 1-[[(4-fluorophenyl)methyl]-1H-benzimidazol-2-yl][1-(trifluoroacetyl)-4-piperidinyl]methanone.

23. A compound according to claim 1 in which said compound is 1-[[(4-fluorophenyl)methyl]-1H-benzimidazol-2-yl][1-(tetrazole acetamide)-4-piperidinyl]methanone.

24. A compound according to claim 1 in which said compound is 1-[[(2-ethoxy)ethyl]-1H-benzimidazol-2-yl][1-(carbomethoxy methoxy ethyl)-4-piperidinyl]methanone.

25. A compound according to claim 1 in which said compound is 1-[[(2-ethoxy)ethyl]-1H-benzimidazol-2-yl][1-(carboxy methoxy ethyl)-4-piperidinyl]methanone.

26. A compound according to claim 1 in which said compound is 1-[(1-carbomethoxy methoxy ethyl)-1H-benzimidazol-2-yl][5-(tetrazolylbutyl)-4-piperidinyl]methanone.

27. A compound according to claim 1 in which said compound is 1-[(1-carboxy methoxy ethyl)-1H-benzimidazol-2-yl][1-(4-tetrazolylbutyl)-4-piperidinyl]methanone.

28. A compound according to claim 1 in which said compound is 1-[(1-carbomethoxy methoxy ethyl)-1H-benzimidazol-2-yl][1-[N-(5-tetrazole)-acetamide]-4-piperidinyl]methanone.

29. A compound according to claim 1 in which said compound is 1-[(1-carboxy methoxy ethyl)-1H-benzimidazol-2-yl][1-[N-(5-tetrazole)-acetamide]-4-piperidinyl]methanone.

30. A compound according to claim 1 in which said compound is 1-[(4-tetrazole butyl]-1H-benzimidazol-2-yl][1-(1carbomethoxy methoxy ethyl)-4-piperidinyl]methanone.

31. A compound according to claim 1 in which said compound is 1-[(4-tetrazole butyl]-1H-benzimidazol-2-yl][1-(1-carboxy methoxy ethyl)-4-piperidinyl]methanone.

32. A compound according to claim 1 in which said compound is 1-[[N-(5-tetrazole)-acetamide]-1H-benzimidazol-2-yl][1-(carbomethoxy methoxy ethyl)-4-piperidinyl]methanone.

33. A compound according to claim 1 in which said compound is 1-[[N-(5-tetrazole)-acetamide]-1H-benzimidazol-2-yl][1-(carboxy methoxy ethyl)-4-piperidinyl]methanone.

34. A compound according to claim 1 in which said compound is 1-[(4-tetrazole butyl]-1H-benzimidazol-2-yl][1-(4-methoxyphenyl ethyl)-4-piperidinyl]methanone.

35. A compound according to claim 1 in which said compound is 1-[(4-tetrazole butyl)-1H-benzimidazol-2-yl][1-(2-ethoxy ethyl)-4-piperidinyl]methanone.

36. A compound according to claim 1 in which said compound is 1-[[N-(5-tetrazole)-acetamide]-1H-benzimidazol-2-yl][1-(4-methoxyphenyl ethyl)-4-piperidinyl]methanone.

37. A compound according to claim 1 in which said compound is 1-[[N-(5-tetrazole)-propionamide]-1H-benzimidazol-2-yl][1-(2-ethoxy ethyl)-4-piperidinyl]methanone.

38. A compound according to claim 1 in which said compound is 1-[(4-tetrazole butyl)-1H-benzimidazol-2-yl][1-(4-tetrazole butyl)-4-piperidinyl]methanone.

39. A compound according to claim 1 in which said compound is 1-[(4-tetrazole butyl)-1H-benzimidazol-2-yl][1-[N-(5-tetrazole)-acetamide]-4-piperidinyl]methanone.

40. A compound according to claim 1 in which said compound is 1-[[N-(5-tetrazole)-acetamide]-1H-benzimidazol-2-yl][1-(4-tetrazole butyl)-4-piperidinyl]methanone.

41. A compound according to claim 1 in which said compound is 1-[[N-(5-tetrazole)-acetamide]-1H-benzimidazol-2-yl][1-[N-(5-tetrazole)-acetamide]-4-piperidinyl]methanone.

42. A compound according to claim 1 in which said compound is 1-[[4-fluorophenyl)methyl]-1H-benzimidazol-2-yl][1-(ethoxycarbonyl)-4-piperidinyl]methanone.

43. A method for the treatment of allergic disease comprising administering a compound according to claim 1 to a patient in need thereof.

44. A composition comprising a compound according to claim 1 in admixture with a pharmaceutically acceptable carrier.

* * * * *